United States Patent
Hah et al.

(10) Patent No.: US 10,301,291 B2
(45) Date of Patent: May 28, 2019

(54) IMIDAZOLE DERIVATIVE HAVING JNK INHIBITORY ACTIVITY AND USE THEREOF

(71) Applicant: SAMJIN PHARMACEUTICAL CO., LTD., Seoul (KR)

(72) Inventors: Jung-Mi Hah, Seoul (KR); Song I Yang, Gyeongsangnam-do (KR); Jung Hun Lee, Gyeonggi-do (KR)

(73) Assignee: SAMJIN PHARMACEUTICAL CO., LTD., Seoul (KR)

( * ) Notice: Subject to any disclaimer, the term of this patent is extended or adjusted under 35 U.S.C. 154(b) by 0 days.

(21) Appl. No.: 16/073,595

(22) PCT Filed: Jan. 25, 2017

(86) PCT No.: PCT/KR2017/000860
§ 371 (c)(1),
(2) Date: Jul. 27, 2018

(87) PCT Pub. No.: WO2017/131425
PCT Pub. Date: Aug. 3, 2017

(65) Prior Publication Data
US 2019/0031645 A1    Jan. 31, 2019

(30) Foreign Application Priority Data

Jan. 29, 2016 (KR) ........................ 10-2016-0011683

(51) Int. Cl.
| | | |
|---|---|---|
| *C07D 405/14* | (2006.01) | |
| *C07D 401/14* | (2006.01) | |
| *C07D 403/04* | (2006.01) | |
| *A61K 31/357* | (2006.01) | |
| *A61K 31/36* | (2006.01) | |
| *A61K 31/506* | (2006.01) | |

(52) U.S. Cl.
CPC .......... *C07D 405/14* (2013.01); *A61K 31/357* (2013.01); *A61K 31/36* (2013.01); *A61K 31/506* (2013.01); *C07D 401/14* (2013.01); *C07D 403/04* (2013.01)

(58) Field of Classification Search
CPC .. C07D 405/14; C07D 401/14; C07D 403/04; A61K 31/357; A61K 31/36; A61K 31/506
See application file for complete search history.

(56) References Cited

U.S. PATENT DOCUMENTS

| | | |
|---|---|---|
| 6,200,977 B1 | 3/2001 | Cushing et al. |
| 6,410,726 B1 | 6/2002 | Powers |
| 2004/0220201 A1 | 11/2004 | Bilodeau et al. |

FOREIGN PATENT DOCUMENTS

| | | |
|---|---|---|
| KR | 1020010029352 | 4/2001 |
| KR | 1020110044544 | 4/2011 |

OTHER PUBLICATIONS

Manley, Peter J. et al., "2,4-Disubstituted Pyrimidines: A Novel Class of KDR Kinase Inhibitors", Bioorganic & Medicinal Chemistry Letters, 2003, pp. 1673-1677, vol. 13.
English language translation of the International Search Report dated May 8, 2017, prepared in International Application No. PCT/KR2017/000860.
International Preliminary Report on Patentability dated Jul. 31, 2018, prepared in International Application No. PCT/KR2017/000860.
English language translation Written Opinion of the ISA dated May 8, 2017, prepared in International Application No. PCT/KR2017/000860.

*Primary Examiner* — Rebecca L Anderson
(74) *Attorney, Agent, or Firm* — Brinks Gilson & Lione

(57) ABSTRACT

The present invention relates to a novel imidazole derivative having a C-Jun N-terminal kinase (JNK) inhibitory activity and a use thereof. A novel imidazole derivative or a pharmaceutically acceptable salt thereof according to the present invention exhibits an excellent inhibitory activity against C-Jun N-terminal kinase (JNK), and thus it is anticipated that a more fundamental approach and target treatment will be possible in the prevention or treatment of degenerative brain nervous system diseases.

13 Claims, No Drawings

IMIDAZOLE DERIVATIVE HAVING JNK INHIBITORY ACTIVITY AND USE THEREOF

This application is a National Stage application of International Application No. PCT/KR2017/000860 filed Jan. 25, 2017. This application also claims priority under 35 U.S.C. § 119 to Korean Patent Application No. 10-2016-0011683, filed Jan. 29, 2016.

TECHNICAL FIELD

The present invention relates to a novel imidazole derivative having a C-Jun N-terminal kinase (JNK) inhibitory activity and a use thereof.

BACKGROUND

In parallel with a recent rise in an aging population, there has been a rapid increase in patients suffering from degenerative brain nervous system diseases. The degenerative brain nervous system diseases may occur due to an aging-induced structural degeneration of brain nerve cells; a secondary symptom caused by adult diseases such as a circulatory disorder, etc.; or physical, mechanical factors such as traffic accidents, industrial accidents, carbon monoxide poisoning, etc., wherein Alzheimer's disease, Parkinson's disease, Huntington's disease, multiple sclerosis, stroke and the like are known as related diseases thereof.

Meanwhile, a C-Jun N-terminal kinase (JNK), which is classified as a serine-threonine kinase, is also called a stress activated protein kinase (SAPK), which is one of the three subtypes of a mitogen activated protein kinase. The JNK is activated in reaction with various stimuli such as cytokine, mitogen, osmotic stress, ultraviolet irradiation, etc., wherein such activated JNK is known to stimulate the phosphorylation of numerous transcription factors including C-Jun of AP-1 as well as the phosphorylation of intracellular proteins such as Bcl2, p53, etc., which are associated with apoptosis. Also, JNK genes form different protein isoforms by means of a splicing process. Out of them, the distribution of JNK3 is concentrated in brain tissues, unlike about 10 other protein isoforms of the same kind, such that there have been various ongoing studies on a relation between the JNK3 and the degenerative brain nervous system diseases.

Particularly, the JNK3 carries out phosphorylation-activation of an amyloid precursor protein (APP), which is a main cause of Alzheimer's disease, such that the APP is located onto a cell membrane and its conversion into beta amyloid is stimulated. By doing so, the beta amyloid is formed, after which its resulting toxicity induces a neuronal cell death. In this case, it is reported that such activation of the JNK3 serves as a main factor. Also, it is seen that a mouse with Familial Alzheimer's diseases (FAD) showed a remarkable decrease in oligomeric beta amyloid and an increase in cognitive ability by means of the removal of the JNK3, and it is also found that a mouse with the JNK3 gene removed therefrom showed an acquisition of resistance to MPTP, a substance for causing Parkinson's disease; obtained an inhibitory effect on adverse reactions to a glutamate analogue, a neurotoxic substance; and the like.

Against such a background, there have been actively ongoing studies to find a JNK3 inhibitor as a novel substance for treating degenerative brain nervous system diseases (Korea Patent Publication No. 2001-0029352), but they have not been enough to produce satisfactory results yet.

DETAILED DESCRIPTION OF THE INVENTION

Technical Problem

The present invention is applied to solve the aforesaid problems, wherein the present inventors have carried out an exemplary research to find a novel substance capable of being developed as a therapeutic agent for degenerative brain nervous system diseases, thus identifying a novel imidazole derivative exhibiting a JNK inhibitory activity and completing the present invention accordingly.

Accordingly, an objective of the present invention is to provide a novel imidazole derivative or a pharmaceutically acceptable salt thereof having a JNK inhibitory activity.

Other objective of the present invention is to provide a method for preparing a novel imidazole derivative having a JNK inhibitory activity.

Another objective of the present invention is to provide a pharmaceutical composition for preventing or treating degenerative brain nervous system diseases, comprising the above imidazole derivative or the pharmaceutically acceptable salt thereof as an effective component.

However, a technical subject to be achieved by the present invention is not limited by the tasks mentioned above, and other tasks not mentioned herein may be clearly understood by those skilled in the art from the following description.

Technical Solution

To achieve the objectives of the present invention above, the present invention provides an imidazole derivative represented by a following Formula 1 or a pharmaceutically acceptable salt thereof.

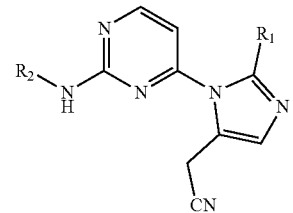

[Formula 1]

In the Formula 1 above, $R_1$ is $C_4$-$C_{10}$ aryl, $C_4$-$C_{10}$ heteroaryl, or $C_4$-$C_{10}$ heterocycloalkyl, wherein $C_4$-$C_{10}$ aryl and $C_4$-$C_{10}$ heteroaryl are ones selected from the group consisting of phenyl, naphthyl, pyrenyl, carbazolyl, benzoxazolyl, benzodioxazolyl, 1,3-benzodioxolyl, 1,4-benzodioxinyl, benzothiazolyl, benzoimidazolyl, benzothiophenyl, quinolinyl, isoquinolinyl, indolyl, benzofuranyl, purinyl and indolizinyl, wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein the $R_1$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino and halogen; and $R_2$ is $C_1$-$C_6$ alkyl, $C_2$-$C_6$ alkenyl, $C_2$-$C_6$ alkynyl, $C_1$-$C_6$ alkoxy, $C_1$-$C_6$ alcohol, $C_3$-$C_{10}$ cycloalkyl, or $C_4$-$C_{10}$ heterocycloalkyl, wherein C$_4$-C$_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein R$_2$ may be unsubstituted or substituted with at least one substituent selected from the group consisting of C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, hydroxy, amino, halogen, C$_2$-C$_{10}$ alkylcarbonyl, and C$_4$-C$_{10}$ cycloalkylcarbonyl.

Also, the present invention, as shown in a following Reaction Formula 1, provides a method for preparing the above imidazole derivative, comprising steps of:

performing a Buchwald amination coupling reaction between a compound of the Formula I and 4-chloro-2-(methylthio)pyrimidine to prepare a compound of a Formula II (Step 1);

oxidizing the compound of the Formula II prepared in the Step 1 above to prepare a compound of a Formula III (Step 2); and substituting a methylsulfonyl group of the compound of the Formula III prepared in the Step 2 above with an amine group to prepare a compound of a Formula IV (Step 3).

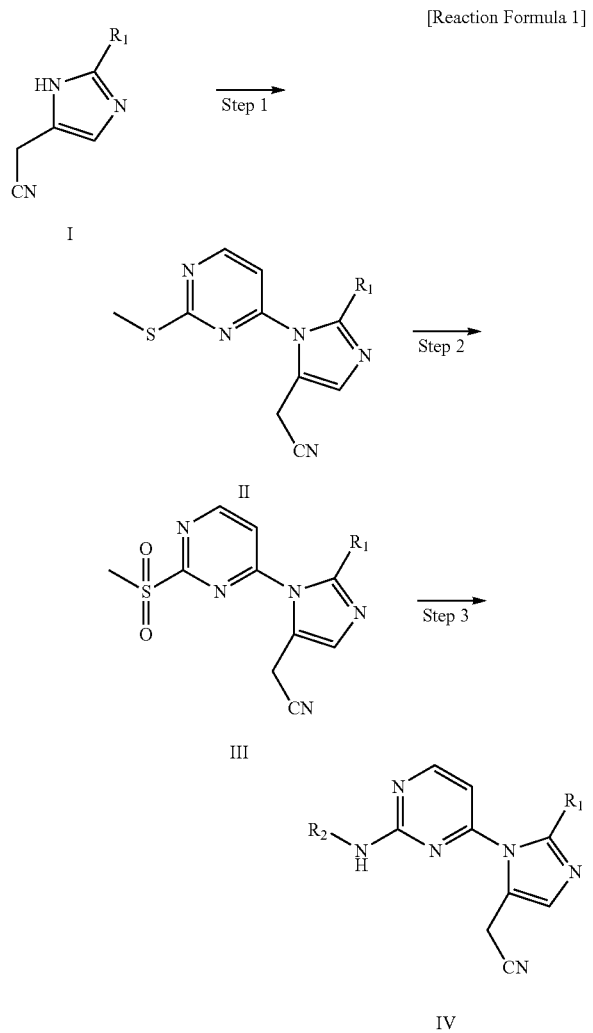

[Reaction Formula 1]

(In the Formulas I to IV above, R$_1$ and R$_2$ are as defined in the Formula 1 of Claim 1.)

Also, the present invention provides a pharmaceutical composition for preventing or treating degenerative brain nervous system diseases, comprising a derivative of the Formula 1 above or a pharmaceutically acceptable salt thereof as an effective component.

In one exemplary embodiment of the present invention, the above degenerative brain nervous system diseases may be selected from the group consisting of Alzheimer's disease, Parkinson's disease, Huntington's disease, multiple sclerosis and stroke.

In other exemplary embodiment of the present invention, the above composition may inhibit an activity of one selected from the group consisting of C-Jun N-terminal kinase 1 (JNK 1), C-Jun N-terminal kinase 2 (JNK 2) and C-Jun N-terminal kinase 3 (JNK 3).

Also, the present invention provides a method for treating degenerative brain nervous system diseases, comprising a step of administering the derivative of the Formula 1 above or the pharmaceutically acceptable salt thereof into an individual.

Moreover, the present invention provides a use of the derivative of the Formula 1 above or the pharmaceutically acceptable salt thereof for treating degenerative brain nervous system diseases.

Advantageous Effects

A novel imidazole derivative or a pharmaceutically acceptable salt thereof according to the present invention exhibits an excellent inhibitory activity against C-Jun N-terminal kinase (JNK), and thus it is anticipated that a pharmaceutical composition comprising the above derivative may be valuably used in the prevention and treatment of degenerative brain nervous system diseases.

Best Mode for Invention

Hereinafter, the present invention will be described in more detail.

The present invention provides an imidazole derivative represented by a following Formula 1 or a pharmaceutically acceptable salt thereof:

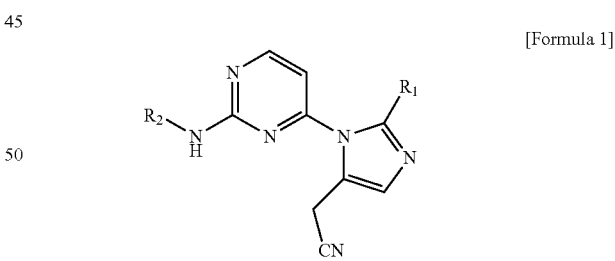

[Formula 1]

In the Formula 1 above,

R$^1$ is C$_4$-C$_{10}$ aryl, C$_4$-C$_{10}$ heteroaryl, or C$_4$-C$_{10}$ heterocycloalkyl, wherein C$_4$-C$_{10}$ aryl and C$_4$-C$_{10}$ heteroaryl are ones selected from the group consisting of phenyl, naphthyl, pyrenyl, carbazolyl, benzoxazolyl, benzodioxazolyl, 1,3-benzodioxolyl, 1,4-benzodioxinyl, benzothiazolyl, benzoimidazolyl, benzothiophenyl, quinolinyl, isoquinolinyl, indolyl, benzofuranyl, purinyl and indolizinyl, wherein C$_4$-C$_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein R$_1$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino and halogen; and $R_2$ is $C_1$-$C_6$ alkyl, $C_2$-$C_6$ alkenyl, $C_2$-$C_6$ alkynyl, $C_1$-$C_6$ alkoxy, $C_1$-$C_6$ alcohol, $C_3$-$C_{10}$ cycloalkyl, or $C_4$-$C_{10}$ heterocycloalkyl, wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein $R_2$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino, halogen, $C_2$-$C_{10}$ alkylcarbonyl, and $C_4$-$C_{10}$ cycloalkylcarbonyl.

Here, a "substituted" group is one in which at least one hydrogen atom is substituted with at least one non-hydrogen atom group, but it is required that valence requirements thereof are met and a chemically stable compound thereof is generated from substitution. In the present specifications, it shall be interpreted that all the substituents may be substituted or unsubstituted, unless explicitly described as "unsubstituted" herein. Each substituent of $R_1$ and $R_2$ of the imidazole derivative according to the present invention may be substituted again with at least one of the substituents defined above.

The "alkyl" generally means linear and branched saturated hydrocarbon groups having the specified number of carbon atoms (e.g., 1 to 12 carbon atoms). Examples of an alkyl group comprise, without limitation, methyl, ethyl, n-propyl, isopropyl, n-butyl, sec-butyl, isobutyl, tert-butyl, n-pentyl, n-hexyl, n-heptyl and the like. The alkyl may be attached to a parent group or a substrate at any ring atom, unless its attachment violates valence requirements. Likewise, the alkyl or alkenyl group may comprise at least one non-hydrogen substituent, unless its attachment violates valence requirements.

The "cycloalkyl" refers to saturated monocyclic and polycyclic hydrocarbon rings generally having the specified number of carbon atoms with a ring (i.e., $C_{3-10}$ cycloalkyl refers to a cycle having 3, 4, 5, 6, 7, 8, 9 or 10 carbon atoms as a ring member). The "heterocycloalkyl" refers to monocyclic and polycyclic hetero rings having 1 to 4 hetero atoms independently selected from nitrogen, oxygen and sulfur, wherein examples of the heterocycloalkyl comprise, without limitation, tetrahydrofuranyl, tetrahydrothiophenyl, pyrrolidinyl, tetrahydropyranyl, tetrahydrothiopyranyl, piperidinyl, dihydrobenzodioxinyl and the like. The cycloalkyl and the heterocycloalkyl may be attached to a parent group or a substrate at any ring atom, unless their attachments violate valence requirements. Likewise, the cycloalkyl and the heterocycloalkyl may comprise at least one non-hydrogen substituent, unless their attachments violate valence requirements.

The "aryl" refers to each of monovalent and divalent aromatic groups including 5- and 6-membered monocyclic aromatic or polycyclic aromatic groups, and the "heteroaryl" refers to each of monovalent and divalent aromatic groups including 5- and 6-membered monocyclic aromatic groups having 1 to 4 hetero atoms independently selected from nitrogen, oxygen and sulfur. Examples of a monocyclic aryl group and a heteroaryl group comprise, without limitation, phenyl, pyridinyl, furanyl, pyrrolyl, thiophenyl, thiazolyl, isothiazolyl, imidazolyl, triazolyl, tetrazolyl, pyrazolyl, oxazolyl, isoxazolyl, pyrazinyl, pyridazinyl, pyrimidinyl, naphthyl, etc. The aryl group and the heteroaryl group also comprise a bicyclic group, a tricyclic group, etc., including the fused 5- and 6-membered rings defined above. Examples of a polycyclic aryl group and a heteroaryl group comprise, without limitation, isoquinolinyl, naphthyl, biphenyl, anthracenyl, pyrenyl, carbazolyl, benzoxazolyl, benzodioxazolyl, benzodioxinyl, benzothiazolyl, benzoimidazolyl, benzothiophenyl, quinolinyl, indolyl, benzofuranyl, furinyl, indolizinyl, etc. The above aryl group and the heteroaryl group may be attached to a parent group or a substrate at any ring atom, unless their attachments violate valence requirements. Likewise, the aryl group and the heteroaryl group may comprise at least one non-hydrogen substituent, unless their substitutions violate valence requirements. The non-hydrogen substituent of the aryl group and the heteroaryl group may be also substituted with an additional non-hydrogen substituent.

The "carbonyl" is —C(O)R'. In the present specifications, the (O) means that oxygen is linked to an atom such as carbon or sulfur by means of a double bond. Here, the R' is a non-hydrogen substituent such as lower alkyl, lower alkoxy, etc. Examples of the carbonyl group comprise, without limitation, 2-methoxyoxoethyl, 3-methoxyoxopropyl, etc. The carbonyl may be attached to a parent group or a substrate at any ring atom, unless its attachment violates valence requirements. Likewise, the carbonyl group may comprise at least one non-hydrogen substituent, unless its attachment violates valence requirements.

The "alkoxy" refers to alkyl-O—, wherein the alkyl is defined above. Examples of the alkoxy group comprise, without limitation, methoxy, ethoxy, etc. The alkoxy may be attached to a parent group or a substrate at any ring atom, unless its attachment violates valence requirements. Likewise, the alkoxy group may comprise at least one non-hydrogen substituent, unless its attachment violates valence requirements.

Also, the imidazole derivative of the Formula 1 above may comprise a racemate thereof or a compound of an isomeric form.

In the imidazole derivative of the Formula 1 of the present invention, $R_1$ is phenyl, naphthyl, 1,3-benzodioxolyl, quinolinyl, 2,3-dihydro-1,4 benzodioxinyl, or benzofuranyl, wherein the $R_1$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino and halogen; and $R_2$ is $C_1$-$C_6$ alcohol, $C_3$-$C_{10}$ cycloalkyl, or $C_4$-$C_{10}$ heterocycloalkyl, wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein $R_2$ may be unsubstituted or substituted with at least one substituent selected from the group consisting of $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, hydroxy, amino, halogen, $C_2$-$C_{10}$ alkylcarbonyl, and $C_4$-$C_{10}$ cycloalkylcarbonyl.

In other exemplary embodiment of the present invention, $R_1$ is phenyl, naphthyl, 1,3-benzodioxolyl, quinolinyl, 2,3-dihydro-1,4 benzodioxinyl, or benzofuranyl, wherein $R_1$ may be unsubstituted or substituted with at least one substituent selected from the group consisting of $C_1$-$C_6$ alkyl, $C_1$-$C_6$ haloalkyl, and halogen; and $R_2$ is $C_1$-$C_6$ alcohol, $C_3$-$C_{10}$ cycloalkyl, or $C_4$-$C_{10}$ heterocycloalkyl, wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, and piperidinyl, and wherein $R_2$ may be unsubstituted or substituted with at least one substituent of $C_2$-$C_{10}$ alkylcarbonyl, or $C_4$-$C_{10}$ cycloalkylcarbonyl.

In another exemplary embodiment of the present invention, $R_1$ is phenyl, naphthyl, 1,3-benzodioxolyl, quinolinyl, 2,3-dihydro-1,4 benzodioxinyl, or benzofuranyl, wherein phenyl may be unsubstituted or substituted with at least one substituent of $C_1$-$C_6$ haloalkyl, or halogen; and $R_2$ is 2-hydroxypropyl, cyclohexyl, tetrahydropyranyl, or piperidinyl, wherein piperidinyl may be unsubstituted or substituted with at least one substituent of $C_4$-$C_{10}$ cycloalkylcarbonyl.

In another exemplary embodiment of the present invention, $R_1$ is phenyl, naphthyl, 1,3-benzodioxolyl, quinolinyl, 2,3-dihydro-1,4 benzodioxinyl, or benzofuranyl, wherein phenyl may be unsubstituted or substituted with at least one substituent selected from the group consisting of fluoro, chloro, and trifluoromethyl; and $R_2$ is 2-hydroxypropyl, cyclohexyl, tetrahydropyranyl, or piperidinyl, wherein piperidinyl may be unsubstituted or substituted with cyclopropanecarbonyl.

In another exemplary embodiment of the present invention, it may be provided that the imidazole derivative of the Formula 1 is 2-(2-(benzo[d][1,3]dioxol-5-yl)-1-(2-(tetrahydro-2H-pyran-4-ylamino)pyrimidine-4-yl)-1H-imidazole-5-yl)acetonitrile; 2-(2-(2,3-dihydrobenzo[b][1,4]dioxin-6-yl)-1-(2-(tetrahydro-2H-pyran-4-ylamino)pyrimidine-4-yl)-1H-imidazole-5-yl)acetonitrile;
2-(2-(quinoline-2-yl)-1-(2-(tetrahydro-2H-pyran-4-ylamino)pyrimidine-4-yl)-1H-imidazole-5-yl) acetonitrile;
2-(2-(naphthalene-2-yl)-1-(2-(tetrahydro-2H-pyran-4-ylamino)pyrimidine-4-yl)-1H-imidazole-5-yl)acetonitrile;
2-(2-(3,4-dichlorophenyl)-1-(2-(tetrahydro-2H-pyran-4-ylamino)pyrimidine-4-yl)-1H-imidazole-5-yl)acetonitrile;
2-(2-(4-fluoro-3-(trifluoromethyl)phenyl)-1-(2-(tetrahydro-2H-pyran-4-ylamino)pyrimidine-4-yl)-1H-imidazole-5-yl)acetonitrile;
2-(2-(benzo[d][1,3]dioxol-5-yl)-1-(2-(cyclohexylamino)pyrimidine-4-yl)-1H-imidazole-5-yl)acetonitrile;
2-(1-(2-(cyclohexylamino)pyrimidine-4-yl)-2-(2,3-dihydrobenzo[b][1,4]dioxin-6-yl)-1H-imidazole-5-yl)acetonitrile;
2-(1-(2-(cyclohexylamino)pyrimidine-4-yl)-2-(quinoline-2-yl)-1H-imidazole-5-yl)acetonitrile;
2-(1-(2-(cyclohexylamino)pyrimidine-4-yl)-2-(naphthalene-2-yl)-1H-imidazole-5-yl)acetonitrile;
2-(1-(2-(cyclohexylamino)pyrimidine-4-yl)-2-(3,4-dichlorophenphenyl)-1H-imidazole-5-yl)acetonitrile;
2-(1-(2-(cyclohexylamino)pyrimidine-4-yl)-2-(4-fluoro-3-(trifluoromethyl)phenyl)-1H-imidazole-5-yl)acetonitrile;
2-(2-(benzo[d][1,3]dioxol-5-yl)-1-(2-(2-hydroxypropylamino)pyrimidine-4-yl)-1H-imidazole-5-yl)acetonitrile;
2-(2-(2,3-dihydrobenzo[b][1,4]dioxin-6-yl)-1-(2-(2-hydroxypropylamino)pyrimidine-4-yl)-1H-imidazole-5-yl)acetonitrile;
2-(1-(2-(2-hydroxypropylamino)pyrimidine-4-yl)-2-(quinoline-2-yl)-1H-imidazole-5-yl)acetonitrile;
2-(1-(2-(2-hydroxypropylamino)pyrimidine-4-yl)-2-(naphthalene-2-yl)-1H-imidazole-5-yl)acetonitrile;
2-(2-(3,4-dichlorophenyl)-1-(2-(2-hydroxypropylamino)pyrimidine-4-yl)-1H-imidazole-5-yl)acetonitrile;
2-(2-(4-fluoro-3-(trifluoromethyl)phenyl)-1-(2-(2-hydroxypropylamino)pyrimidine-4-yl)-1H-imidazole-5-yl)acetonitrile;
2-(2-(benzo[d][1,3]dioxol-5-yl)-1-(2-(piperidine-3-ylamino)pyrimidine-4-yl)-1H-imidazole-5-yl) acetonitrile2-(2-(benzo[d][1,3]dioxol-5-yl)-1-(2-(piperidine-3-ylamino)pyrimidine-4-yl)-1H-imidazole-5-yl) acetonitrile;
2-(2-(2,3-dihydrobenzo[b][1,4]dioxin-6-yl)-1-(2-(piperidine-3-ylamino)pyrimidine-4-yl)-1H-imidazole-5-yl)acetonitrile;
2-(1-(2-(piperidine-3-ylamino)pyrimidine-4-yl)-2-(quinoline-2-yl)-1H-imidazole-5-yl)acetonitrile;
2-(2-(naphthalene-2-yl)-1-(2-(piperidine-3-ylamino)pyrimidine-4-yl)-1H-imidazole-5-yl)acetonitrile;
2-(2-(3,4-dichlorophenyl)-1-(2-(piperidine-3-ylamino)pyrimidine-4-yl)-1H-imidazole-5-yl)acetonitrile;
2-(2-(4-fluoro-3-(trifluoromethyl)phenyl)-1-(2-(piperidine-3-ylamino)pyrimidine-4-yl)-1H-imidazole-5-yl)acetonitrile;
2-(2-(benzo[d][1,3]dioxol-5-yl)-1-(2-(1-(cyclopropanecarbonyl)piperidine-3-ylamino)pyrimidine-4-yl)-1H-imidazole-5-yl)acetonitrile;
2-(1-(2-(1-(cyclopropanecarbonyl)piperidine-3-ylamino)pyrimidine-4-yl)-2-(2,3-dihydrobenzo[b][1,4]dioxin-6-yl)-1H-imidazole-5-yl)acetonitrile;
2-(1-(2-(1-(cyclopropanecarbonyl)piperidine-3-ylamino)pyrimidine-4-yl)-2-(quinoline-2-yl)-1H-imidazole-5-yl)acetonitrile;
2-(1-(2-(1-(cyclopropanecarbonyl)piperidine-3-ylamino)pyrimidine-4-yl)-2-(naphthalene-2-yl)-1H-imidazole-5-yl)acetonitrile;
2-(1-(2-(1-(cyclopropanecarbonyl)piperidine-3-ylamino)pyrimidine-4-yl)-2-(3,4-dichlorophenyl)-1H-imidazole-5-yl)acetonitrile;
2-(1-(2-(1-(cyclopropanecarbonyl)piperidine-3-ylamino)pyrimidine-4-yl)-2-(4-fluoro-3-(trifluoromethyl)phenyl)-1H-imidazole-5-yl)acetonitrile; or
2-(2-(benzofuran-5-yl)-1-(2-(1-cyclopropanecarbonyl)piperidine-3-ylamino)pyrimidine-4-yl)-1H-imidazole-5-yl) acetonitrile.

Meanwhile, the above compound of the present invention may be used in a form of pharmaceutically acceptable salt, wherein an acid-addition salt formed by means of pharmaceutically acceptable free acid is useful as the salt.

The acid-addition salt formed by means of pharmaceutically acceptable free acid is useful as the salt, the term used herein. The acid-addition salt is obtained from inorganic acids such as hydrochloric acid, nitric acid, phosphoric acid, sulfuric acid, hydrobromic acid, hydroiodic acid, nitrous acid or phosphorous acid; and non-toxic organic acid such as aliphatic mono and dicarboxylate, phenyl-substituted alkanoate, hydroxy alkanoate and alkanedioate, aromatic acids, aliphatic and aromatic sulphonic acids. Such pharmaceutically non-toxic salts comprise sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1, 4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate or mandelate.

The acid-addition salt according to the present invention may be prepared by means of a conventional method, for example, in such a way that compounds represented by the Formulas 1 to 4 are dissolved in an excessive amount of acid aqueous solution, and then a resulting salt is deposited by means of a water miscible organic solvent, for example, methanol, ethanol, acetone or acetonitrile. Also, such acid-addition salt may be also prepared by evaporating a solvent or an excessive amount of acid from a resulting mixture, and then dehydrating a resulting residue or carrying out a suction-filtration of a resulting precipitated salt.

Also, the pharmaceutically acceptable metal salt may be made by means of a base. Alkali metal or alkali earth metal salt is obtained, for example, by dissolving a compound in an excessive amount of alkali metal hydroxide or alkali earth metal hydroxide solution, filtering an undissolved compound salt, and evaporating and dehydrating a remaining solution. At this time, as the metal salt, it is pharmaceutically appropriate to prepare sodium, potassium or calcium salts. Also, silver salt corresponding thereto is obtained in such a way that alkali metal or alkali earth metal salt is reacted with an appropriate silver salt (ex. silver nitrate).

Also, the compound of the present invention comprises a pharmaceutically acceptable salt as well as all the salts, isomers, hydrates and solvates, which may be prepared by means of a conventional method.

The imidazole derivative of the Formula 1 above according to the present invention may be prepared by means of several methods.

In a specific embodiment,
as shown in a following Reaction Formula 1,
the imidazole derivative of the Formula 1 may be prepared by a method, comprising steps of: performing a Buchwald amination coupling reaction between a compound of the Formula I and 4-chloro-2-(methylthio)pyrimidine to prepare a compound of a Formula II (Step 1); oxidizing the compound of the Formula II prepared in the Step 1 above to prepare a compound of a Formula III (Step 2); and substituting a methylsulfonyl group of the compound of the Formula III prepared in the Step 2 above with an amine group to prepare a compound of a Formula IV (Step 3). Here, if $R_2$ of the compound of the Formula IV is tetrahydropyran, cyclohexane, 2-hydroxypropane or tert-butylpiperidine-1-carboxylate, each one is a compound of a Formula IV-1, IV-2, IV-3 or IV-4.

[Reaction Formula 1]

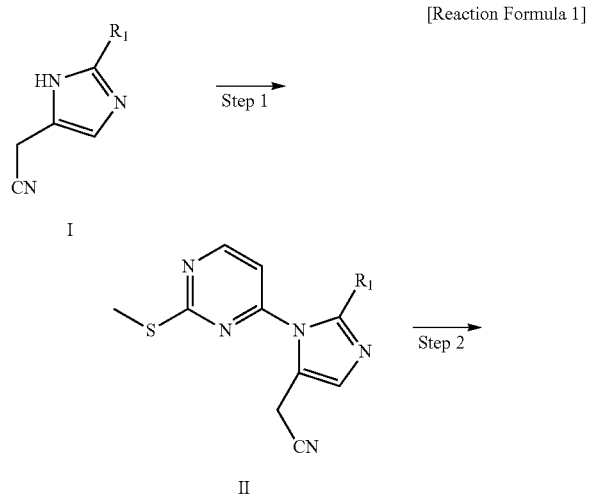

In one exemplary embodiment, the imidazole derivative of the Formula 1 may be obtained through steps of: performing a Buchwald amination coupling reaction between a compound 7 of the present invention and 4-chloro-2-(methylthio)pyrimidine to prepare a compound 8 (Step 1); oxidizing a compound 8 prepared in the Step 1 above to prepare a compound 9 (Step 2); and substituting a methylsulfonyl group of the compound 9 prepared in the Step 2 above with an amine group to prepare compounds 10 to 13 (Step 3).

Also, as shown in a following Reaction Formula 2,
the imidazole derivative of the Formula 1 may be prepared by means of a method, further comprising a step of performing a deprotection of the compound of the Formula IV-4 prepared in the Step 3 above to prepare a compound of a Formula V (Step 4).

[Reaction Formula 2]

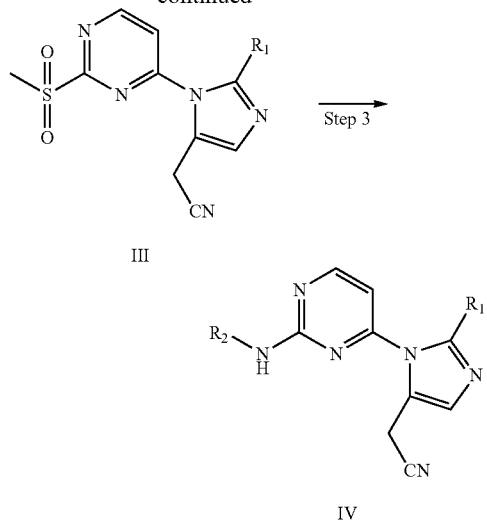

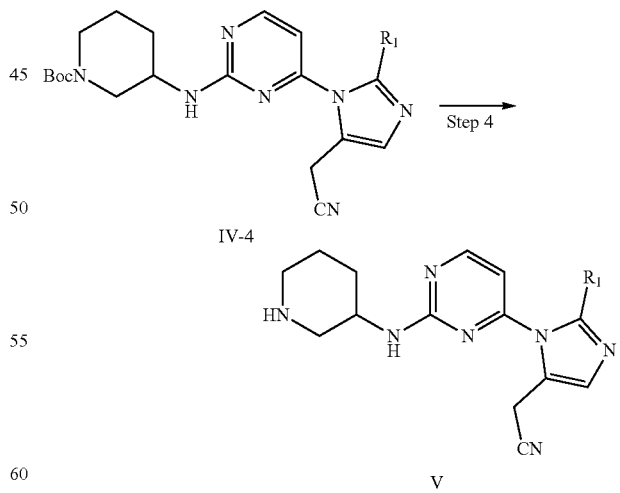

In one exemplary embodiment, the imidazole derivative of the Formula 1 may be obtained through a step of dissolving the compound 13 of the present invention in 1,4-dioxane and then treating a resulting solution with hydrochloric acid to prepare a compound 14 (Step 4).

Also, as shown in a following Reaction Formula 3, the imidazole derivative of the Formula 1 may be obtained by means of a method, further comprising a step of acylating the compound of the Formula V prepared in the Step 4 above to prepare a compound of a Formula VI (Step 5).

[Reaction Formula 3]

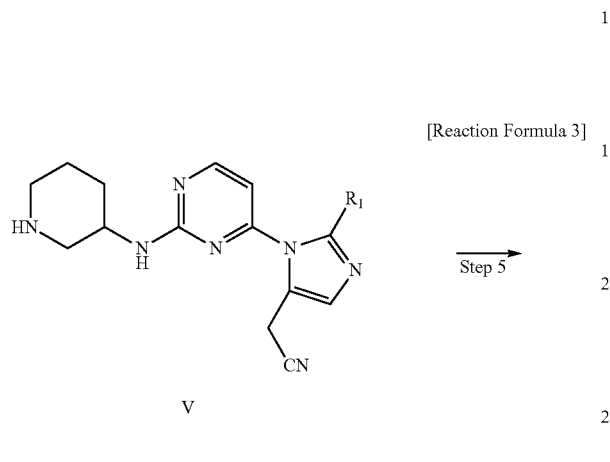

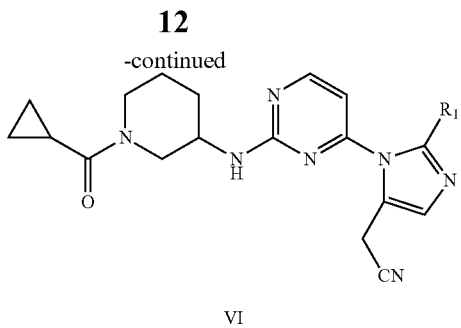

VI

In one exemplary embodiment, the imidazole derivative of the Formula 1 may be obtained through a step of acylating the compound 14 of the present invention to prepare a compound 15 (Step 5).

In one embodiment of the present invention, it was identified that compounds 10a to 12f, and compounds 14a to 15g, prepared according to a synthesis strategy of a following Reaction Formula 4, showed an excellent inhibitory activity against JNK3, in particular that a compound 15d did not show an inhibitory activity against other protein kinases, but was capable of selectively inhibiting an activity of JNK1/2/3, thus it was identified that they might be valuably used as an effective substance for treating degenerative brain nervous system diseases. (See Experimental Examples 1 to 2.)

[Reaction Formula 4]

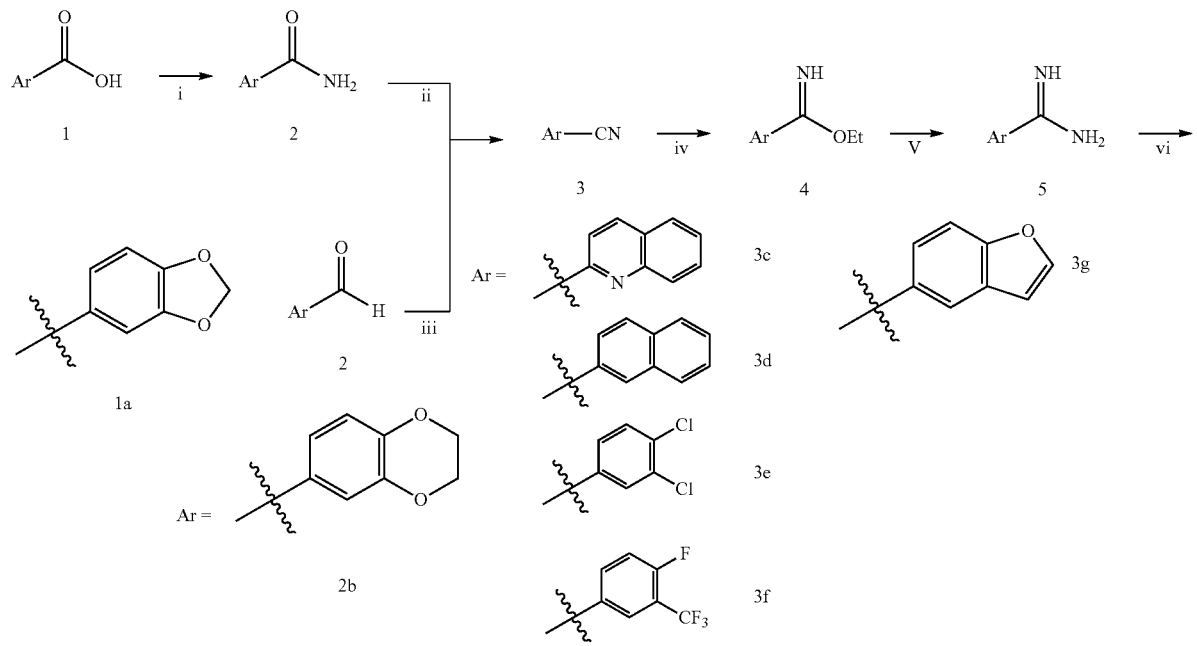

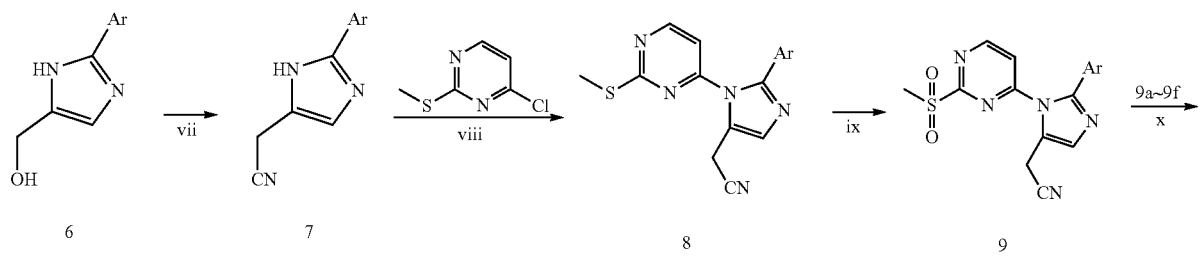

-continued

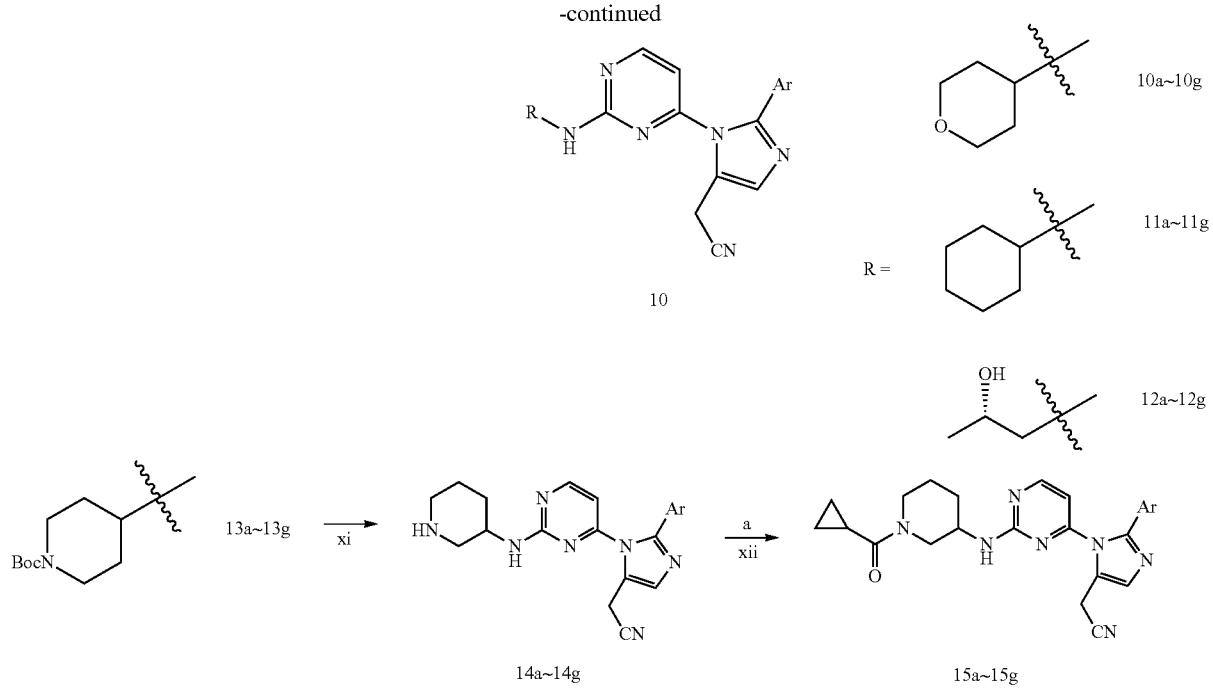

Accordingly, the present invention provides a pharmaceutical composition for preventing or treating degenerative brain nervous system diseases, comprising the imidazole derivative of the Formula 1 above or the pharmaceutically acceptable salt thereof as an effective component; a use of the imidazole derivative of the Formula 1 above or the pharmaceutically acceptable salt thereof for treating the above diseases; and a method for treating the above diseases, comprising an administration of a therapeutically effective amount of the compound of the Formula 1 above or the pharmaceutically acceptable salt thereof into an object.

As used herein, the term "prevention" means all the acts to inhibit degenerative brain nervous system diseases or delay an occurrence thereof by means of an administration of the pharmaceutical composition according to the present invention.

As used herein, the term "treatment" means all the acts, by which a symptom of degenerative brain nervous system diseases changes for the better or takes a favorable turn by means of an administration of the pharmaceutical composition according to the present invention.

The "degenerative brain nervous system diseases," which are the diseases to be prevented or treated by means of the composition of the present invention, may comprise, without limitation, any diseases caused by a brain damage, but preferably may be Alzheimer's disease, Parkinson's disease, Huntington's disease, multiple sclerosis or stroke.

The pharmaceutical composition of the present invention may comprise a pharmaceutically acceptable carrier in addition to the effective component. At this time, the pharmaceutically acceptable carrier is one conventionally used in preparing a formulation, wherein such carrier comprises lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil and the like, but not limited thereto. In addition to the above components, the pharmaceutical composition of the present invention may further comprise lubricant, humectant, sweetening agent, flavoring agent, emulsifier, suspending agent, preservative, etc.

The pharmaceutical composition of the present invention may be orally or parenterally administered (for example, intravenously, subcutaneously, intraperitoneally or locally applied) according to a targeted method, wherein a dosage may vary depending on a patient's condition and weight, a disease's degree, a drug type, an administration route and time, but it may be appropriately selected by those skilled in the art.

The pharmaceutical composition of the present invention is administered in a pharmaceutically effective amount thereof. According to the present invention, the pharmaceutically effective amount means an amount sufficient to treat a disease at a reasonable benefit/risk ratio applicable to medical treatment, wherein a level of such effective amount may depend on factors including a patient's disease type, severity, a drug's activity, sensitivity to the drug, an administration time, an administration route and an excretion rate, a treatment period and a simultaneously used drug as well as other factors well known in the medical field. The pharmaceutical composition according to the present invention may be administered as an individual therapeutic agent or in combination with other therapeutic agents, administered sequentially or simultaneously with conventional therapeutic agents, and administered with a single dose or a multi dose. It is important to administer an amount of such composition that is capable of gaining a maximum effect with a minimum amount without a side effect, considering all the factors above, wherein it may be easily decided by those skilled in the art.

Particularly, the effective amount of the pharmaceutical composition of the present invention may vary depending on a patient's age, gender, condition, weight, an absorption of an active component in vivo, an inactive ratio and excretion rate, a disease type and a concomitant drug, wherein it may be generally administered in an amount of 0.001 to 150 mg, preferably 0.01 to 100 mg per 1 kg of body weight, every day or every other day, or administered in such a way that the amount is divided into 1 to 3 times a day. However, it may be increased or decreased according to an administration route, severity of obesity, gender, weight, age, etc., thus the above dosage is not construed to limit the scope of the present invention by any means.

In the present invention, the "individual" means an object, which requires a treatment for diseases, more particularly, humans or mammals such as non-human primates, mouse, dog, cat, horse, cow and the like.

Hereinafter, preferred Examples will be suggested for better understanding of the present invention. However, the following Examples are provided only for the purpose of illustrating the present invention, and thus the present invention is not limited thereto.

<Preparation Example 1> Preparation of ethyl 1,3-benzodioxolyl-5-carboxyimidate (Compound 4a)

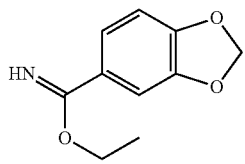

Step 1. Preparation of 1,3-benzodioxolyl-5-carboxyamide 1,3-benzodioxolyl-5-carboxylic acid (compound 1a, 1 g, 6 mmol) was mixed in thionyl chloride ($SOCl_2$, 4.4 ml), and then a resulting solution was heated at 80° C. until the above compound disappeared from TLC. After a reaction was completed, the resulting solution was cooled down to room temperature, then solvent was removed therefrom under vacuum, then a compound obtained therefrom and methanol (6 ml) dissolved in 7N ammonia were mixed in ethanol (9 ml), and then the above resulting mixture was stirred at room temperature for 12 hours. After a completion of the reaction was identified, the resulting mixture was concentrated under vacuum, diluted with ether, and stirred until a resulting product is separated into a solid. Then, the solid product was filtered and sequentially washed with ether and hexane solvents, so as to obtain 1,3-benzodioxolyl-5-carboxamide (compound 2a) (95% yield).

a white solid (95%); $^1$H NMR (400 MHz, DMSO) δ7.83 (s, 1H), 7.46 (dd, J=8.1, 1.7 Hz, 1H), 7.40 (d, J=1.7 Hz, 1H), 6.96 (d, J=8.1 Hz, 1H), 6.08 (s, 2H); LRMS (ESI) m/z calcd for $C_8H_7NO_3$ [M+H]+: 166, Found 166.

Step 2. Preparation of 1,3-benzodioxolyl-5-carbonitrile

The compound 2a (6.66 mmol) obtained in the Step 1 above was mixed in phosphoryl trichloride ($POCl_3$, 19 ml), and then the above mixture was stirred at 95° C. for 2 hours. After a reaction was completed, the resulting mixture was cooled down to room temperature, then solvent was removed therefrom under vacuum, then an extraction from the above concentrated mixture was performed with ethyl acetate (EtOAc) and 10% $K_2CO_3$ aqueous solution, and then a resulting organic layer was washed with water and brine. Then, a resulting residue was dehydrated with magnesium sulfate anhydrous ($MgSO_4$), and then solvent was evaporated therefrom, so as to obtain 1,3-benzodioxolyl-5-carbonitrile (compound 3a) (83% yield).

a white solid (83%); $^1$H NMR (400 MHz, DMSO) δ 7.43 (d, J=1.4 Hz, 1H), 7.40 (dd, J=8.0, 1.7 Hz, 1H), 7.10 (d, 1H), 6.17 (s, 2H); LRMS (ESI) m/z calcd for $C_8H_5NO_2$ [M+H]+: 148, Found 148.

Step 3. Preparation of ethyl 1,3-benzodioxolyl-5-carboxyimidate

The compound 3a obtained in the Step 2 above was dissolved in ethanol (3.4 ml), then acetyl chloride (AcCl, 3.1 ml) was slowly added into a resulting solution at 0° C., and then a resulting mixture was stirred at room temperature for 24-48 hours. After the above compounds 3a to 3f completely disappeared from TLC, a resulting residue was concentrated under vacuum, and then the above concentrated mixture was diluted with ether, and stirred until a solid product was separated therefrom. Then, the above solid product was filtered and sequentially washed with ether and hexane solvents, so as to obtain ethyl 1,3-benzodioxolyl-5-carboxyimidate (compound 4a) (99% yield).

a white solid (99%); $^1$H NMR (400 MHz, DMSO) δ 7.75 (dd, J=8.3, 2.0 Hz, 1H), 7.70 (d, J=1.9 Hz, 1H), 7.18 (d, J=8.3 Hz, 1H), 6.23 (s, 2H), 4.58 (q, J=7.0 Hz, 2H), 1.46 (t, J=7.0 Hz, 3H).); LRMS (ESI) m/z calcd for $C_{10}H_{11}NO_3$ [M+H]+: 194, Found 194.

<Preparation Example 2> Preparation of ethyl 1,4-benzodioxane-6-carboxyimidate (Compound 4b)

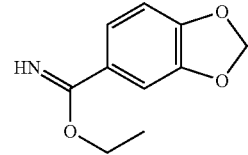

Step 1. Preparation of 1,4-benzodioxane-6-carbonitrile 1,4-benzodioxane-6-carboaldehyde (compound 2b, 500 mg, 3.05 mmol), hydroxylamine hydrochloride (255 mg, 3.7 mmol), and sodium sulfate (434 mg, 3.05 mmol) were dissolved in DMF (15.3 ml), and then a resulting solution was stirred at 170° C. for 4 hours. Then, sodium sulfate was filtered, then an extraction was performed with ethyl acetate (EtOAc), and then an organic layer was washed with water and brine. A resulting product was dehydrated with magnesium sulfate anhydrous ($MgSO_4$), and then solvent was evaporated therefrom, so as to obtain 1,4-benzodioxane-6-carbonitrile (compound 3b) (yield 81%).

a white solid (81%); $^1$H NMR (400 MHz, DMSO) δ 7.39 (d, J=2.0 Hz, 1H), 7.30 (dd, J=8.4, 2.0 Hz, 1H), 7.03 (d, J=8.4 Hz, 1H), 4.35-4.32 (m, 2H), 4.31-4.27 (m, 2H); LRMS (ESI) m/z calcd for $C_9H_7NO_2$ [M+H]+: 162, Found 162.

Step 2. Preparation of ethyl 1,4-benzodioxane-6-carboxyimidate

The compound 3b obtained in the Step 1 above was used to obtain ethyl 1,4-benzodioxane-6-carboxyimidate (compound 4b) by means of the same method as shown in Preparation Example 1—Step 3 above.

a white solid (99%); $^1$H NMR (400 MHz, DMSO) δ 11.70 (s, 1H), 7.70 (d, J=2.3 Hz, 1H), 7.64 (dd, J=8.6, 2.3 Hz, 1H), 7.11 (d, J=8.6 Hz, 1H), 4.57 (q, J=7.0 Hz, 2H), 4.40-4.37 (m, 2H), 4.34-4.31 (m, 2H), 1.46 (t, J=7.0 Hz, 3H); LRMS (ESI) m/z calcd for $C_{11}H_{13}NO_3$ [M+H]+: 208, Found 208.

Compounds of following Preparation Examples 3 to 6 were obtained by means of the same method as shown in the Preparation Example 1 above (wherein 1,3-benzodioxolyl was replaced with quinolinyl, naphthylyl, 3,4-dichlorophenyl, 4-fluoro-3-(trifluoromethyl)phenyl, respectively).

<Preparation Example 3> Preparation of ethyl quinoline-2-carbimidate (Compound 4c)

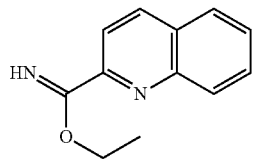

a yellow solid (99%); $^1$H NMR (400 MHz, DMSO) δ 12.03 (s, 1H), 8.76 (d, J=8.4 Hz, 1H), 8.22 (t, J=9.2 Hz, 3H), 7.99 (ddd, J=8.5, 6.9, 1.4 Hz, 1H), 7.86 (ddd, J=8.1, 6.9, 1.2 Hz, 1H), 4.78 (q, J=7.0 Hz, 2H), 1.55 (t, J=7.0 Hz, 3H); LRMS (ESI) m/z calcd for $C_{12}H_{12}N_2O$ [M+H]+: 201, Found 201.

<Preparation Example 4> Preparation of ethyl 2-naphthylimidate (Compound 4d)

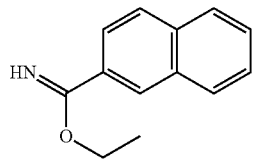

a white solid (99%); $^1$H NMR (400 MHz, DMSO) δ 8.90 (s, 1H), 8.14 (t, J=3.9 Hz, 3H), 8.07 (d, J=8.2 Hz, 1H), 7.79-7.73 (m, 1H), 7.67-7.72 (m, J=8.1, 7.0, 1.2 Hz, 1H), 4.71 (q, J=7.0 Hz, 2H), 3.70 (s, 1H), 1.53 (t, J=7.0 Hz, 3H); LRMS (ESI) m/z calcd for $C_{13}H_{13}NO$ [M+H]+: 200, Found 200.

<Preparation Example 5> Preparation of ethyl 3,4-dichlorobenzimidate (Compound 4e)

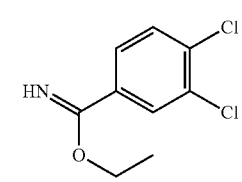

a white solid (99%); $^1$H NMR (400 MHz, DMSO) δ 8.41 (s, 1H), 8.06 (d, J=8.0 Hz, 1H), 7.93 (d, J=8.2 Hz, 1H), 4.60 (q, J=6.4 Hz, 2H), 1.46 (t, J=5.9 Hz, 3H).); LRMS (ESI) m/z calcd for $C_9H_9Cl_2NO$ [M+H]+: 219, Found 219.

<Preparation Example 6> Preparation of ethyl 4-fluoro-3-(trifluoromethyl)benzimidate (Compound 4f)

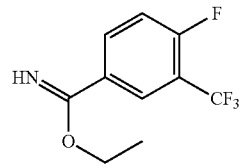 [SMILES: CCOC(=N)c1ccc(F)c(C(F)(F)F)c1]

a white solid (84%); $^1$H NMR (400 MHz, DMSO) δ 8.57 (dd, J=6.6, 2.0 Hz, 1H), 8.54-8.47 (m, 1H), 7.84 (t, 1H), 4.63 (q, J=7.0 Hz, 2H), 1.48 (t, J=7.0 Hz, 3H); LRMS (ESI) m/z calcd for $C_{10}H_9F_4NO$ [M+H]+: 236, Found 236.

<Preparation Example 7> Preparation of benzo[d][1,3]dioxol-5-carboxyimidamide (Compound 5a)

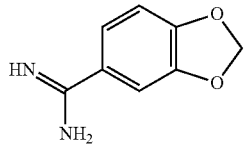 [SMILES: N=C(N)c1ccc2c(c1)OCO2]

The compound 4a (4.25 mmol) obtained in the Preparation Example 1 above and methanol (4.25 ml) dissolved in 7N ammonia were mixed in ethanol (4.25 ml), and then the above mixture was stirred at room temperature for 12 hours. After the compound 4a completely disappeared from TLC, a resulting residue was concentrated under vacuum, and then the above concentrated mixture was diluted with ether, and stirred until a solid product was separated therefrom. Then, the above solid product was filtered and sequentially washed with ether and hexane solvents, so as to obtain a crystalized compound 5a.

a white solid (81%); $^1$H NMR (400 MHz, DMSO) δ 9.07 (s, 4H), 7.46 (dd, J=8.2 Hz, 1H), 7.43 (d, J=1.8 Hz, 1H), 7.16 (d, J=8.2 Hz, 1H), 6.19 (s, 2H); LRMS (ESI) m/z calcd for $C_8H_9ClN_2O_2$ [M+H]+: 201, Found 201.

Compounds of following Preparation Examples 8 to 12 were obtained by means of the same method as shown in the Preparation Example 7 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Preparation Example 8> Preparation of 2,3-dihydrobenzo[b][1,4]dioxin-6-carboxyimidamide (Compound 5b)

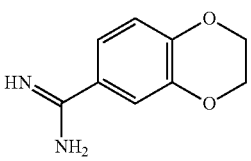 [SMILES: N=C(N)c1ccc2c(c1)OCCO2]

a white solid (92%); ¹H NMR (400 MHz, DMSO) δ 9.22 (s, 4H), 9.09 (s, 3H), 7.45 (d, J=2.3 Hz, 2H), 7.40 (dd, J=8.5, 2.4 Hz, 2H), 7.08 (d, J=8.5 Hz, 2H), 4.37-4.33 (m, 4H), 4.33-4.29 (m, 4H); LRMS (ESI) m/z calcd for C$_9$H$_{11}$ClN$_2$O$_2$ [M+H]+: 216, Found 216.

<Preparation Example 9> Preparation of quinolin-2-carboxyimidamide (Compound 5c)

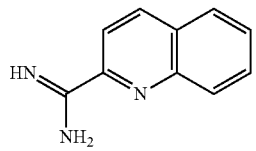 [SMILES: N=C(N)c1ccc2ccccc2n1]

a white solid (93%); ¹H NMR (400 MHz, DMSO) δ 9.77 (s, 3H), 8.76 (d, J=8.6 Hz, 1H), 8.35 (d, J=8.6 Hz, 1H), 8.23-8.15 (dd, J=12.0, 8.4 Hz, 2H), 8.00-7.93 (m, 1H), 7.83 (m, J=7.5 Hz, 1H), 7.33 (s, 2H).); LRMS (ESI) m/z calcd for C$_{10}$H$_{10}$ClN$_3$ [M+H]+: 208, Found 208.

<Preparation Example 10> Preparation of 2-naphthyimidamide (Compound 5d)

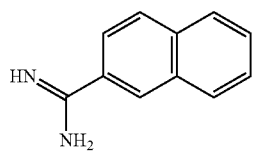 [SMILES: N=C(N)c1ccc2ccccc2c1]

a white solid (83%); ¹H NMR (400 MHz, DMSO) δ 9.63 (s, 5H), 9.44 (s, 5H), 8.57 (d, J=1.5 Hz, 3H), 8.15 (d, J=87 Hz, 3H), 8.06-8.10 (t, J=8.4 Hz, 6H), 7.85-7.90 (dd, J=8.6, 1.9 Hz, 3H), 7.66-7.75 (tdd, J=14.6, 6.9, 1.4 Hz, 6H).); LRMS (ESI) m/z calcd for C$_{11}$H$_{11}$N$_2$ [M+H]+: 207, Found 207.

<Preparation Example 11> Preparation of 3,4-dichlorobenzimidamide (Compound 5e)

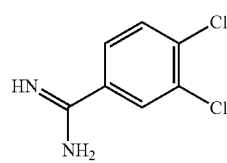 [SMILES: N=C(N)c1ccc(Cl)c(Cl)c1]

a white solid (70%); ¹H NMR (400 MHz, DMSO) δ 9.19 (s, 4H), 8.18 (s, 1H), 7.94 (d, 1H), 7.85 (d, 1H); LRMS (ESI) m/z calcd for C$_7$H$_7$Cl$_3$N$_2$ [M+H]+: 226, Found 226.

<Preparation Example 12> Preparation of 4-fluoro-3-(trifluoromethyl)benzimidamide (Compound 5f)

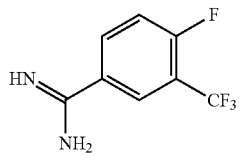

a white solid (95%); ¹H NMR (400 MHz, DMSO) δ 9.32 (s, 4H), 8.31 (dd, J=6.6, 2.0 Hz, 1H), 8.29-8.24 (m, 1H), 7.82 (t, 1H); LRMS (ESI) m/z calcd for C$_8$H$_6$F$_4$N$_2$ [M+H]+: 207, Found 207.

<Preparation Example 13> Preparation of (2-(benzo[d][1,3]dioxol-5-yl)-1H-imidazole-5-yl)methanol (Compound 6a)

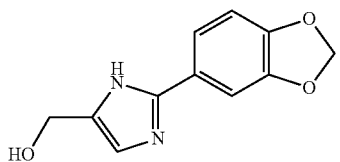

The compound 5a (3.1 mmol) obtained in the Preparation Example 7 above, 1,3-dihydroxyacetone dimer (3.34 mmol), NH$_4$OH (12.2 ml), and NH$_4$Cl (16.2 mmol) were stirred at 80° C. for 2 hours. After the compound 5a completely disappeared from TLC, a reaction mixture was cooled down to room temperature, and then methylene chloride (CH$_2$Cl$_2$) was inserted thereinto, so as to separate a layer there/from. After a solid product produced on an organic layer was filtered, the resulting solid product was washed with methylene chloride (CH$_2$Cl$_2$) and crystalized, so as to obtain a compound 6a.

a brown solid (38%); ¹H NMR (400 MHz, DMSO) δ 12.20 (s, 1H), 7.43 (dd, J=5.9, 1.7 Hz, 2H), 6.97 (d, 1H), 6.93 (s, 1H), 6.05 (s, 2H), 4.94 (s, 1H), 4.40 (d, J=3.3 Hz, 2H); LRMS (ESI) m/z calcd for C$_{11}$H$_{10}$N$_2$O$_3$ [M+H]+: 219, Found 219.

Compounds of following Preparation Examples 14 to 18 were obtained by means of the same method as shown in the Preparation Example 13 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Preparation Example 14> Preparation of (2-(2,3-dihydrobenzo[b][1,4]dioxin-6-yl)-1H-imidazole-5-yl)methanol (Compound 6b)

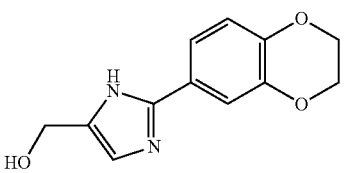

a brown solid (54%); $^1$H NMR (400 MHz, DMSO) δ 12.17 (s, 1H), 7.41 (d, J=2.1 Hz, 1H), 7.38 (d, J=2.1 Hz, 1H), 6.91 (s, 1H), 6.89 (dd, J=8.2, 0.4 Hz, 1H), 4.93 (s, 1H), 4.39 (s, 2H), 4.26 (s, 4H); LRMS (ESI) m/z calcd for $C_{12}H_{12}N_2O_3$ [M+H]+: 233, Found 233.

<Preparation Example 15> Preparation of (2-(quinoline-2-yl)-1H-imidazole-5-yl)methanol (Compound 6c)

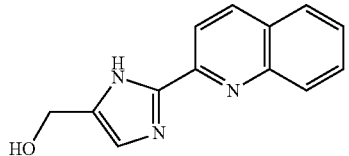 [SMILES: OCc1cnc(-c2ccc3ccccc3n2)[nH]1]

a yellow solid (60%); $^1$H NMR (400 MHz, DMSO) δ 12.76 (s, 1H), 8.41 (d, J=8.6 Hz, 1H), 8.19 (d, J=8.6 Hz, 1H), 8.04 (d, J=8.7 Hz, 1H), 7.98 (d, J=8.2, 1.0 Hz, 1H), 7.81-7.76 (m, J=8.4, 6.9, 1.4 Hz, 1H), 7.62-7.56 (m, J=8.1, 6.9, 1.2 Hz, 1H), 7.15 (s, 1H), 4.98 (s, 1H), 4.50 (dd, J=30.0, 5.1 Hz, 2H). LRMS (ESI) m/z calcd for $C_{13}H_{11}N_3O$ [M+H]+: 226, Found 226.

<Preparation Example 16> Preparation of (2-(naphthalene-2-yl)-1H-imidazole-5-yl)methanol (Compound 6d)

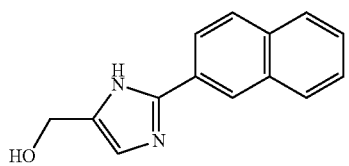 [SMILES: OCc1cnc(-c2ccc3ccccc3c2)[nH]1]

a white solid (50%); $^1$H NMR (400 MHz, DMSO) δ 12.56 (s, 1H), 8.44 (s, 1H), 8.10 (dd, J=8.6, 1.3 Hz, 1H), 7.96 (d, J=8.7 Hz, 1H), 7.94-7.89 (m, J=6.1 Hz, 2H), 7.58-7.46 (m, J=6.8, 1.4 Hz, 2H), 7.06 (s, 1H), 4.98 (s, 1H), 4.47 (d, J=5.3 Hz, 2H); LRMS (ESI) m/z calcd for $C_{14}H_{12}N_2O$[M+H]+: 225, Found 225.

<Preparation Example 17> Preparation of (2-(3,4-dichlorophenyl)-1H-imidazole-5-yl)methanol (Compound 6e)

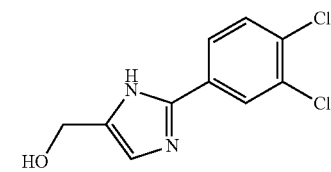 [SMILES: OCc1cnc(-c2ccc(Cl)c(Cl)c2)[nH]1]

a brown solid (58%); $^1$H NMR (400 MHz, DMSO) δ 12.57 (s, 1H), 8.15 (dd, 1H), 7.90 (d, J=1.9 Hz, 1H), 7.69 (d, J=8.5 Hz, 1H), 7.03 (d, J=90.6 Hz, 1H), 5.07 (d, J=103.1 Hz, 1H), 4.43 (d, J=19.6 Hz, 2H). LRMS (ESI) m/z calcd for $C_{10}H_8Cl_2N_2O$ [M+H]+: 244, Found 244.

<Preparation Example 18> Preparation of (2-(4-fluoro-3-(trifluoromethyl)phenyl)-1H-imidazole-5-yl)methanol (Compound 6f)

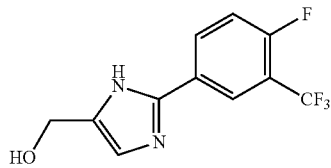

a brown solid (80%); $^1$H NMR (400 MHz, DMSO) δ 12.74 (s, 1H), 8.32 (dd, J=6.9, 2.0 Hz, 1H), 8.29-8.23 (m, 1H), 7.60 (dd, J=10.3, 9.1 Hz, 1H), 7.05 (s, 1H), 5.06 (s, 1H), 4.44 (s, 2H); LRMS (ESI) m/z calcd for $C_{11}H_8F_4N_2O$ [M+H]+: 261, Found 261.

<Preparation Example 19> Preparation of 2-(2-(benzo[d][1,3]dioxol-5-yl)-1H-imidazole-5-yl)acetonitrile (Compound 7a)

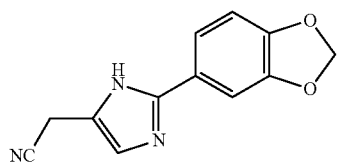 [SMILES: N#CCc1cnc(-c2ccc3c(c2)OCO3)[nH]1]

Thionyl chloride (3.5 ml) was mixed in the compound 6a (4.8 mmol) obtained in the Preparation Example 13 above, and then a resulting solution was heated at 80° C. until the above compound disappeared from TLC. After a reaction was completed, a resulting residue was cooled down to room temperature, then solvent was removed therefrom under vacuum, and then dimethyl sulfoxide (24 ml) was inserted into a resulting compound obtained therefrom and sodium cyanide (24 mmol), and stirred at room temperature for 24 hours. After a completion of the reaction was identified, an extraction from a reaction mixture was performed with ethyl acetate (EtOAc), and then an organic layer was washed with water and brine. Then, a resulting residue was dehydrated with magnesium sulfate anhydrous (MgSO4), then solvent was evaporated therefrom, and then a resulting product was separated and purified by means of a column chromatography (EA:HEX=1:1), so as to obtain a compound 7a.

a yellow solid (43%); $^1$H NMR (400 MHz, DMSO) δ 12.38 (s, 1H), 7.44 (dd, 1H), 7.42 (s, 1H), 7.14 (s, 1H), 6.99 (dd, J=7.5, 1.1 Hz, 1H), 6.06 (s, 2H), 3.87 (s, 2H); LRMS (ESI) m/z calcd for $C_{12}H_9N_3O_2$ [M+H]+: 228, Found 228.

Compounds of following Preparation Examples 20 to 24 were obtained by means of the same method as shown in the Preparation Example 19 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Preparation Example 20> Preparation of 2-(2-(2,3-dihydrobenzo[b][1,4]dioxin-6-yl)-1H-imidazole-5-yl)acetonitrile (Compound 7b)

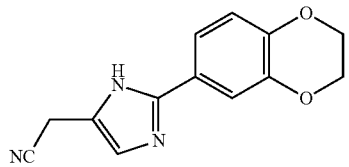 [SMILES: N#CCc1cnc(-c2ccc3c(c2)OCCO3)[nH]1]

a yellow solid (32%); $^1$H NMR (400 MHz, DMSO) δ 12.36 (s, 1H), 7.40 (d, 1H), 7.39 (d, 1H), 7.11 (s, 1H), 6.91 (dd, 1H), 4.27 (s, 4H), 3.87 (s, 2H); LRMS (ESI) m/z calcd for $C_{13}H_{11}N_3O_2$ [M+H]+: 242, Found 242.

<Preparation Example 21> Preparation of 2-(2-(quinoline-2-yl)-1H-imidazole-5-yl)acetonitrile (Compound 7c)

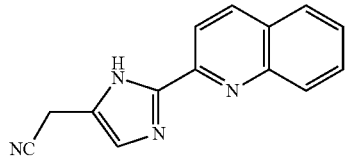 [SMILES: N#CCc1cnc(-c2ccc3ccccc3n2)[nH]1]

a yellow solid (36%); $^1$H NMR (400 MHz, DMSO) δ 13.00 (s, 1H), 8.45 (d, J=8.4 Hz, 1H), 8.19 (d, J=8.6 Hz, 1H), 8.05 (d, J=8.3 Hz, 1H), 8.00 (d, J=8.2 Hz, 1H), 7.83-7.77 (m, J=8.4, 6.9, 1.5 Hz, 1H), 7.64-7.58 (m, J=8.1, 6.9, 1.1 Hz, 1H), 7.27 (s, 1H), 3.97 (d, J=0.6 Hz, 2H); LRMS (ESI) m/z calcd for $C_{14}H_{10}N_4$ [M+H]+: 235, Found 235.

<Preparation Example 22> Preparation of 2-(2-(naphthalene-2-yl)-1H-imidazole-5-yl)acetonitrile (Compound 7d)

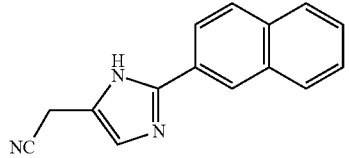 [SMILES: N#CCc1cnc(-c2ccc3ccccc3c2)[nH]1]

a yellow solid (74%); $^1$H NMR (400 MHz, DMSO) δ 12.76 (s, 1H), 8.46 (s, 1H), 8.09 (dd, J=8.6, 1.6 Hz, 1H), 7.99 (d, J=9.0 Hz, 1H), 7.97-7.90 (m, 2H), 7.59-7.49 (m, 2H), 7.27 (s, 1H), 3.95 (s, 2H); LRMS (ESI) m/z calcd for $C_{15}H_{11}N_3$ [M+H]+: 234, Found 234.

<Preparation Example 23> Preparation of 2-(2-(3,4-dichlorophenyl)-1H-imidazole-5-yl)acetonitrile (Compound 7e)

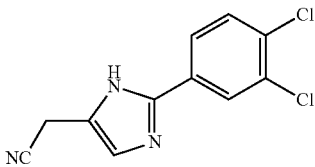

a yellow solid (75%); $^1$H NMR (400 MHz, DMSO) δ 12.78 (s, 1H), 8.13 (d, J=2.0 Hz, 1H), 7.89 (dd, J=8.5, 2.1 Hz, 1H), 7.72 (d, J=8.5 Hz, 1H), 7.28 (s, 1H), 3.92 (s, 2H); LRMS (ESI) m/z calcd for $C_{11}H_7Cl_2N_3$ [M+H]+: 253, Found 253.

<Preparation Example 24> Preparation of 2-(2-(4-fluoro-3-(trifluoromethyl)phenyl)-1H-imidazole-5-yl)acetonitrile (Compound 7f)

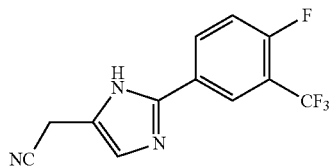

a yellow solid (43%); $^1$H NMR (400 MHz, DMSO) δ 12.83 (s, 1H), 8.29 (d, J=7.0 Hz, 1H), 8.25 (dd, J=5.6, 3.1 Hz, 1H), 7.63 (dd, 1H), 7.29 (s, 1H), 3.92 (s, 2H); LRMS (ESI) m/z calcd for $C_{12}H_7F_4N_3$ [M+H]+: 270, Found 270.)

<Preparation Example 25> Preparation of 2-(2-(benzo[d][1,3]dioxol-5-yl)-1-(2-(methylthio)pyrimidine-4-yl)-1H-imidazole-5-yl)acetonitrile (Compound 8a)

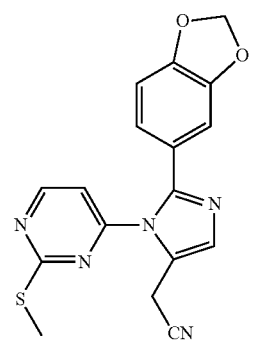 [SMILES: CSc1nccc(-n2c(CC#N)cnc2-c2ccc3c(c2)OCO3)n1]

The compound 7a (1.3 mmol) obtained in the Preparation Example 19 above, 4-iodo-2-(methylthio)pyrimidine (320 mg, 1.3 mmol), palladium (II) acetate (Pd(oAc)$_2$, 88 mg, 0.13 mmol), X-Phos (62 mg, 0.13 mmol), and $CS_2CO_3$3 were purged along with nitrogen, and then toluene (13 mL) was added into a resulting solution, and mixed together. After the above mixture was sonicated for 5 minutes, the resulting mixture was heated up to 130° C. under the condition that nitrogen is present therein, and then the resulting mixture was stirred without nitrogen at 130° C. for 3 hours. After the resulting mixture was cooled down to room temperature, the reaction mixture was filtered with a celite pad, then solvent was removed therefrom under vacuum, and then a resulting residue was separated and purified by means of a column chromatography (DCM:MEOH=40:1), so as to obtain a compound 8a.

a yellow solid (27%); $^1$H NMR (400 MHz, DMSO) δ 8.65 (d, J=5.4 Hz, 1H), 7.79 (s, 1H), 6.99 (dd, J=3.5, 1.9 Hz, 2H), 6.96 (d, J=8.0 Hz, 1H), 6.87 (dd, J=8.1, 1.7 Hz, 1H), 6.08 (s, 2H), 3.99 (d, J=0.8 Hz, 2H), 2.30 (s, 3H); LRMS (ESI) m/z calcd for $C_{17}H_{13}N_5O_2S$ [M+H]+: 352, Found 352.

Compounds of following Preparation Examples 26 to 30 were obtained by means of the same method as shown in the Preparation Example 25 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Preparation Example 26> Preparation of 2-(2-(2,3-dihydrobenzo[b][1,4]dioxin-6-yl)-1-(2-(methylthio)pyrimidine-4-yl)-1H-imidazole-5-yl)acetonitrile (Compound 8b)

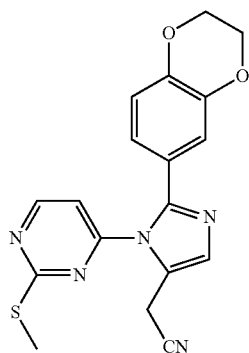 [SMILES: CSc1nccc(-n2c(CC#N)cnc2-c2ccc3c(c2)OCCO3)n1]

a yellow solid (33%); $^1$H NMR (400 MHz, CDCl$_3$) δ 8.43 (d, J=5.4 Hz, 1H), 7.73 (s, 1H), 7.01 (s, 1H), 6.90 (d, J=1.1 Hz, 2H), 6.58 (d, J=5.4 Hz, 1H), 4.34-4.31 (m, 2H), 4.30-4.26 (m, 2H), 3.86 (s, 2H), 2.54 (s, 3H); LRMS (ESI) m/z calcd for $C_{18}H_{15}N_5O_2S$ [M+H]+: 366, Found 366.

<Preparation Example 27> Preparation of 2-(1-(2-(methylthio)pyrimidine-4-yl)-2-(quinoline-2-yl)-1H-imidazole-5-yl)acetonitrile (Compound 8c)

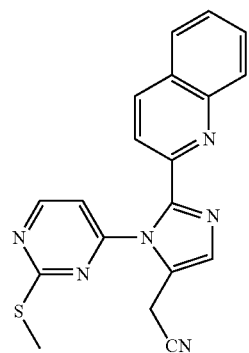 [SMILES: CSc1nccc(-n2c(CC#N)cnc2-c2ccc3ccccc3n2)n1]

a yellow solid (24%); $^1$H NMR (400 MHz, CDCl$_3$) δ 8.47 (d, J=5.4 Hz, 1H), 8.28 (d, J=8.5 Hz, 1H), 8.10 (d, J=8.5 Hz, 1H), 7.85 (d, J=7.7 Hz, 1H), 7.73 (d, J=8.4 Hz, 1H), 7.70-7.65 (m, 2H), 7.60-7.54 (m, J=8.1, 6.7, 1.4 Hz, 1H), 6.82 (d, J=5.4 Hz, 1H), 3.86 (d, J=0.9 Hz, 2H), 2.41 (s, 3H); LRMS (ESI) m/z calcd for $C_{19}H_{14}N_6S$ [M+H]+: 359, Found 359.

<Preparation Example 28> Preparation of 2-(1-(2-(methylthio)pyrimidine-4-yl)-2-(naphthalene-2-yl)-1H-imidazole-5-yl)acetonitrile (Compound 8d)

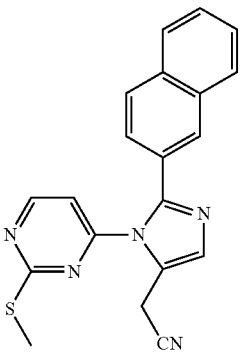 [SMILES: CSc1nccc(-n2c(CC#N)cnc2-c2ccc3ccccc3c2)n1]

a yellow solid (27%); $^1$H NMR (400 MHz, CDCl$_3$) δ 8.33 (d, J=5.4 Hz, 1H), 8.05 (s, 1H), 7.88 (dd, J=7.0, 1.6 Hz, 2H), 7.85 (s, 1H), 7.80 (s, 1H), 7.60-7.52 (m, 2H), 7.42 (dd, J=8.5, 1.7 Hz, 1H), 6.51 (d, J=5.4 Hz, 1H), 3.88 (d, J=0.9 Hz, 2H), 2.43 (s, 3H); LRMS (ESI) m/z calcd for $C_{20}H_{15}N_5S$ [M+H]+: 358, Found 358.

<Preparation Example 29> Preparation of 2-(2-(3,4-dichlorophenyl)-1-(2-(methylthio)pyrimidine-4-yl)-1H-imidazole-5-yl)acetonitrile (Compound 8e)

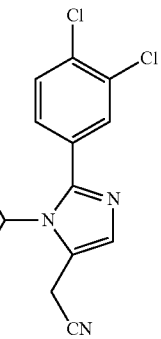

a yellow solid (35%); $^1$H NMR (400 MHz, CDCl$_3$) δ 8.42 (d, J=5.4 Hz, 1H), 7.61 (s, 1H), 7.58 (d, J=2.0 Hz, 1H), 7.40 (d, J=8.3 Hz, 1H), 7.15 (dd, J=8.3, 2.0 Hz, 1H), 6.53 (d, J=5.4 Hz, 1H), 3.74 (d, J=0.8 Hz, 2H), 2.37 (s, 3H); LRMS (ESI) m/z calcd for $C_{16}H_{11}Cl_2N_5S$ [M+H]+: 377, Found 377.

<Preparation Example 30> Preparation of 2-(2-(4-fluoro-3-(trifluoromethyl)phenyl)-1-(2-(methylthio)pyrimidine-4-yl)-1H-imidazole-5-yl) acetonitrile (Compound 8f)

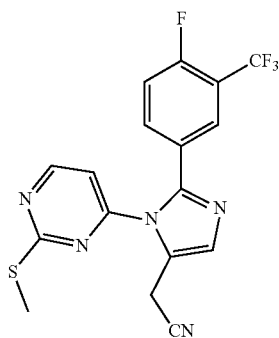 [SMILES: CSc1nccc(-n2c(CC#N)cnc2-c2ccc(F)c(C(F)(F)F)c2)n1]

a yellow solid (23%); $^1$H NMR (400 MHz, MeOD) δ 8.61 (d, J=5.4 Hz, 1H), 7.84 (dd, J=6.9, 2.2 Hz, 1H), 7.82 (dd, J=2.2, 1.3 Hz, 1H), 7.73-7.68 (m, 1H), 7.42 (dd, 1H), 7.11 (d, J=5.4 Hz, 1H), 3.93 (d, J=0.9 Hz, 2H), 2.17 (s, 3H); LRMS (ESI) m/z calcd for $C_{17}H_{11}F_4N_5S$ [M+H]+: 394, Found 394.

<Preparation Example 31> Preparation of 2-(2-(benzo[d][1,3]dioxol-5-yl)-1-(2-(methylsulfonyl)pyrimidine-4-yl)-1H-imidazole-5-yl)acetonitrile (Compound 9a)

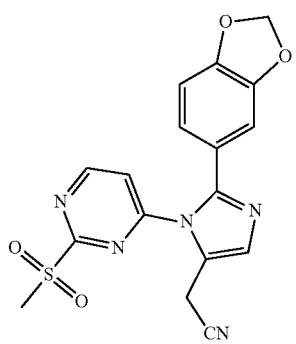 [SMILES: CS(=O)(=O)c1nccc(-n2c(CC#N)cnc2-c2ccc3c(c2)OCO3)n1]

The compound 8a (1 mmol) obtained in the Preparation Example 25 above and potassium peroxomonosulfate (5 mmol) were mixed in a solvent (5 ml), which was mixed at a ratio of methanol:water=1:1, and then the above mixture was stirred at room temperature for 1 hour. After the above compound completely disappeared from TLC, methanol was concentrated under vacuum. The above concentrated mixture was diluted with an addition of water thereinto, and stirred until a solid product was separated therefrom. The above solid product was filtered, sequentially washed with ether and hexane solvents, and crystalized compound 9a was obtained.

a white solid (46%); $^1$H NMR (400 MHz, DMSO) δ 9.06 (d, J=5.6 Hz, 1H), 7.92 (s, 1H), 7.70 (dd, J=8.2 Hz, 1H), 7.61 (d, J=1.7 Hz, 1H), 7.54 (d, J=5.6 Hz, 1H), 6.97 (s, 1H), 6.16 (s, 2H), 4.03 (s, 2H), 3.24 (s, 3H); LRMS (ESI) m/z calcd for $C_{17}H_{13}N_5O_4S$ [M+H]+: 384, Found 384.

Compounds of following Preparation Examples 32 to 36 were obtained by means of the same method as shown in the Preparation Example 31 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Preparation Example 32> Preparation of 2-(2-(2,3-dihydrobenzo[b][1,4]dioxin-6-yl)-1-(2-(methylsulfonyl)pyrimidine-4-yl)-1H-imidazole-5-yl)acetonitrile (Compound 9b)

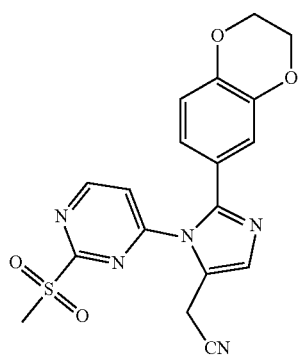 [SMILES: CS(=O)(=O)c1nccc(-n2c(CC#N)cnc2-c2ccc3c(c2)OCCO3)n1]

a white solid; 1H NMR (400 MHz, DMSO) δ 11.57 (s, 1H), 8.90 (d, J=5.8 Hz, 1H), 8.38 (d, J=5.8 Hz, 1H), 7.64 (d, 1H), 7.62 (dd, J=8.5 Hz, 1H), 7.00 (d, J=8.4 Hz, 1H), 4.36-4.32 (m, J=4.6 Hz, 2H), 4.32-4.28 (m, J=4.3 Hz, 2H), 3.60 (s, 2H), 3.41 (s, 3H); LRMS (ESI) m/z calcd for $C_{18}H_{15}N_5N_5O_4S$ [M+H]+: 398, Found 398.

<Preparation Example 33> Preparation of 2-(1-(2-(methylsulfonyl)pyrimidine-4-yl)-2-(quinoline-2-yl)-1H-imidazole-5-yl)acetonitrile (Compound 9c)

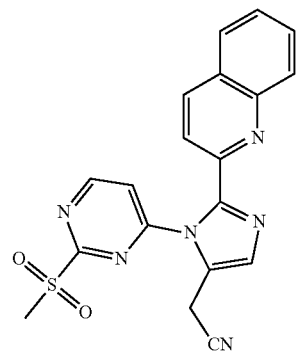 [SMILES: CS(=O)(=O)c1nccc(-n2c(CC#N)cnc2-c2ccc3ccccc3n2)n1]

a yellow solid (73%); 1H NMR (400 MHz, DMSO) δ 9.17 (d, J=5.4 Hz, 1H), 8.53 (d, J=8.7 Hz, 1H), 8.20 (d, J=8.6 Hz, 1H), 8.03 (d, J=8.2 Hz, 1H), 7.98 (d, J=5.4 Hz, 1H), 7.94 (s, 1H), 7.73-7.68 (m, 1H), 7.64-7.59 (m, J=10.9, 4.1 Hz, 1H), 7.39 (d, J=7.7 Hz, 1H), 4.14 (d, J=0.8 Hz, 2H), 3.25 (s, 3H); LRMS (ESI) m/z calcd for $C_{19}H_{14}N_6O_2S$ [M+H]+: 391, Found 391.

<Preparation Example 34> Preparation of 2-(1-(2-(methylsulfonyl)pyrimidine-4-yl)-2-(naphthalene-2-yl)-1H-imidazole-5-yl)acetonitrile (Compound 9d)

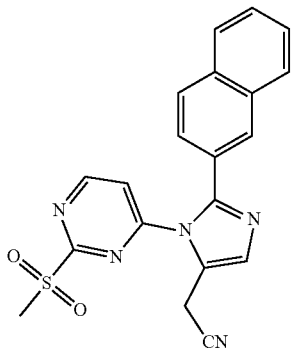 [SMILES: CS(=O)(=O)c1nccc(-n2c(CC#N)cnc2-c2ccc3ccccc3c2)n1]

a yellow solid (86%); 1H NMR (400 MHz, DMSO) δ 9.05 (d, J=5.6 Hz, 1H), 8.17 (d, J=1.4 Hz, 1H), 8.03 (s, 1H), 8.01-7.97 (m, J=5.1, 4.0 Hz, 2H), 7.96 (d, J=8.6 Hz, 1H), 7.63 (d, J=5.6 Hz, 1H), 7.61-7.54 (m, 3H), 4.10 (d, J=0.8 Hz, 2H), 3.02 (s, 3H); LRMS (ESI) m/z calcd for $C_{20}H_{15}N_5O_2S$ [M+H]+: 390, Found 390.

<Preparation Example 35> Preparation of 2-(2-(3,4-dichlorophenyl)-1-(2-(methylsulfonyl)pyrimidine-4-yl)-1H-imidazole-5-yl)acetonitrile (Compound 9e)

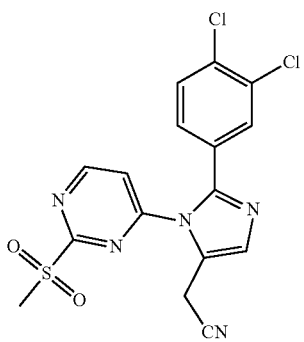 [SMILES: CS(=O)(=O)c1nccc(-n2c(CC#N)cnc2-c2ccc(Cl)c(Cl)c2)n1]

a white solid (83%); $^1$H NMR (400 MHz, DMSO) δ 9.13 (d, J=5.6 Hz, 1H), 8.03 (s, 1H), 7.84 (d, J=2.0 Hz, 1H), 7.80 (d, J=5.6 Hz, 1H), 7.68 (d, J=8.4 Hz, 1H), 7.47 (dd, J=8.4, 2.1 Hz, 1H), 4.07 (d, J=0.8 Hz, 2H), 3.14 (s, 3H); LRMS (ESI) m/z calcd for $C_{16}H_{11}Cl_2N_5O_2S$ [M+H]+: 409, Found/ 409.

<Preparation Example 36> Preparation of 2-(2-(4-fluoro-3-(trifluoromethyl)phenyl)-1-(2-(methylsulfonyl)pyrimidine-4-yl)-1H-imidazole-5-yl)acetonitrile (Compound 9f)

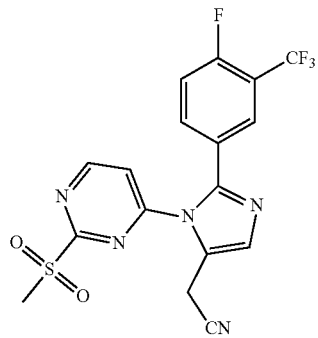 [SMILES: CS(=O)(=O)c1nccc(-n2c(CC#N)cnc2-c2ccc(F)c(C(F)(F)F)c2)n1]

a yellow solid (57%); $^1$H NMR (400 MHz, DMSO) δ 9.14 (d, J=5.6 Hz, 1H), 8.07 (s, 1H), 7.96 (dd, J=6.8, 1.7 Hz, 1H), 7.91-7.82 (m, J=5.2 Hz, 2H), 7.56 (dd, 1H), 4.08 (s, 2H), 3.11 (s, 3H); LRMS (ESI) m/z calcd for $C_{17}H_{11}F_4N_5O_2S$ [M+H]+: 426, Found 426.

<Example 1> Preparation of 2-(2-(benzo[d][1,3]dioxol-5-yl)-1-(2-(tetrahydro-2H-pyran-4-ylamino)pyrimidine-4-yl)-1H-imidazole-5-yl)acetonitrile (Compound 10a)

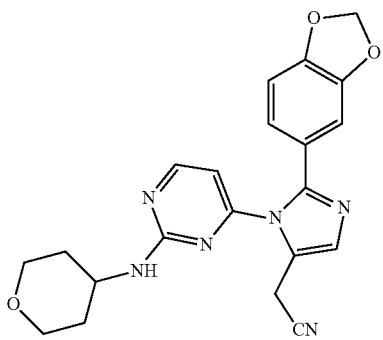 [SMILES: N#CCc1cnc(-c2ccc3c(c2)OCO3)n1-c1ccnc(NC2CCOCC2)n1]

The compound 9a (0.03 mmol) obtained in the Preparation Example 31 above and tetrahydro-2H-pyran-4-amine (0.06 mmol) were stirred in THF (0.3 ml) at 60° C. for 5 hours. After the compound 9a completely disappeared, the reaction mixture was cooled down to room temperature, and concentrated under vacuum. The above concentrated mixture was separated and purified by means of a column chromatography (DCM:MEOH=40:1), so as to obtain a compound 10a.

a yellow solid (84%); $^1$H NMR (400 MHz, DMSO) δ 8.34 (d, 1H), 7.68 (d, 1H), 7.61 (s, 1H), 7.54 (d, 1H), 6.96 (d, J=8.3 Hz, 1H), 6.86 (dd, J=8.0, 1.7 Hz, 1H), 6.06 (s, 2H), 4.20 (s, 1H), 3.96 (s, 2H), 3.84-3.73 (m, 2H), 3.18-3.10 (m, 1H), 1.50-1.41 (m, 2H), 1.40-1.29 (m, 2H), 0.88-0.81 (m, 2H); LRMS (ESI) m/z calcd for $C_{21}H_{20}N_6O_3$ [M+H]+: 405, Found 405.

Compounds of following Examples 2 to 6 were obtained by means of the same method as shown in the Example 1 above (1,3-benzodioxolyl was substituted with 2,3-dihydro- 1,4 benzodioxinyl, quinolinyl, naphthylyl, 3,4-dichlorophenyl and 4-fluoro-3-(trifluoromethyl)phenyl, respectively).

<Example 2> Preparation of 2-(2-(2,3-dihydrobenzo[b][1,4]dioxin-6-yl)-1-(2-(tetrahydro-2H-pyran-4-ylamino)pyrimidine-4-yl)-1H-imidazole-5-yl)acetonitrile (Compound 10b)

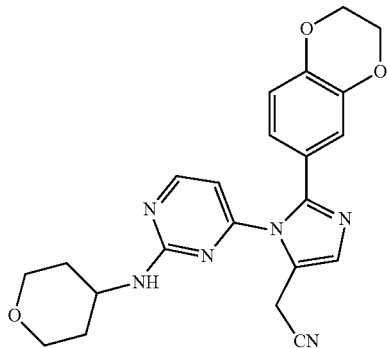 [SMILES: N#CCc1cnc(-c2ccc3c(c2)OCCO3)n1-c1ccnc(NC2CCOCC2)n1]

a white solid (33%); 1H NMR (400 MHz, DMSO) δ 8.35 (d, 1H), 7.59 (s, 1H), 7.54 (s, 1H), 6.88 (d, J=8.6 Hz, 1H), 6.83 (dd, J=8.4, 1.8 Hz, 1H), 6.37 (d, J=159.2 Hz, 1H), 4.29-4.19 (m, J=2.9 Hz, 4H), 3.96 (s, 2H), 3.76 (s, 1H), 3.19-3.08 (m, 1H), 1.55-1.41 (m, 2H), 1.39-1.26 (m, 2H), 1.27-1.17 (m, 2H), 0.88-0.77 (m, J=8.7, 5.5, 2.1 Hz, 2H); LRMS (ESI) m/z calcd for $C_{22}H_{22}N_6O_3$ [M+H]+: 419, Found 419.

<Example 3> Preparation of 2-(2-(quinoline-2-yl)-1-(2-(tetrahydro-2H-pyran-4-ylamino)pyrimidine-4-yl)-1H-imidazole-5-yl) acetonitrile (Compound 10C)

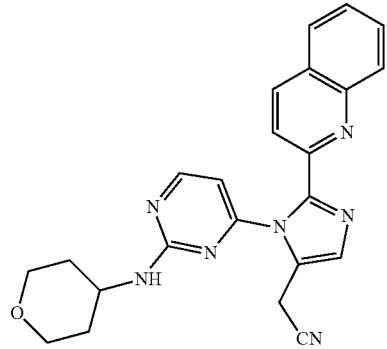 [SMILES: N#CCc1cnc(-c2ccc3ccccc3n2)n1-c1ccnc(NC2CCOCC2)n1]

a yellow solid (35%); 1H NMR (400 MHz, MeOD) δ 8.46 (d, J=8.5 Hz, 1H), 8.33 (d, J=5.2 Hz, 1H), 7.99 (d, J=8.1 Hz, 1H), 7.89 (s, 1H), 7.84-7.72 (m, 3H), 7.67-7.61 (m, J=7.4 Hz, 1H), 6.73 (d, 1H), 3.97 (d, J=0.8 Hz, 2H), 3.53 (s, 1H), 2.05-2.00 (m, J=9.6 Hz, 2H), 1.92-1.71 (m, J=30.9 Hz, 2H), 1.61-1.47 (m, 2H), 1.20-1.06 (m, 3H), 0.92-0.85 (m, 1H); LRMS (ESI) m/z calcd for C23H21N7O [M+H]+: 412, Found 412.

<Example 4> Preparation of 2-(2-(naphthalene-2-yl)-1-(2-(tetrahydro-2H-pyran-4-ylamino)pyrimidine-4-yl)-1H-imidazole-5-yl)acetonitrile (Compound 10d)

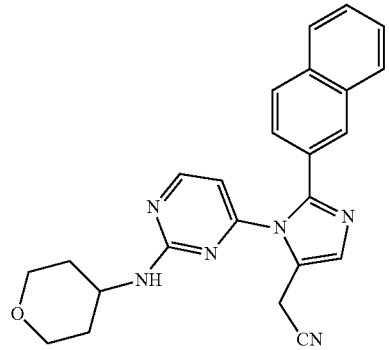 [SMILES: N#CCc1cnc(-c2ccc3ccccc3c2)n1-c1ccnc(NC2CCOCC2)n1]

a white solid (35%); $^1$H NMR (400 MHz, CDCl$_3$) δ 8.10 (d, J=4.7 Hz, 1H), 8.00 (s, 1H), 7.81 (d, J=2.3 Hz, 1H), 7.78 (d, J=8.4 Hz, 2H), 7.57 (s, 1H), 7.53-7.46 (m, J=6.9, 1.7 Hz, 2H), 7.34 (d, J=8.1 Hz, 1H), 6.38 (d, 1H), 4.68 (s, 1H), 3.80 (d, J=0.9 Hz, 2H), 3.65-3.54 (m, 1H), 3.33-3.19 (m, 14H), 2.92-2.77 (m, 1H), 1.53-1.39 (m, 2H), 1.34 (d, J=19.3 Hz, 2H), 1.21-1.16 (m, 1H), 0.84-0.75 (m, 1H); LRMS (ESI) m/z calcd for $C_{24}H_{22}N_6O$ [M+H]+: 411, Found 411.

<Example 5> Preparation of 2-(2-(3,4-dichlorophenyl)-1-(2-(tetrahydro-2H-pyran-4-ylamino)pyrimidine-4-yl)-1H-imidazole-5-yl)acetonitrile (Compound 10e)

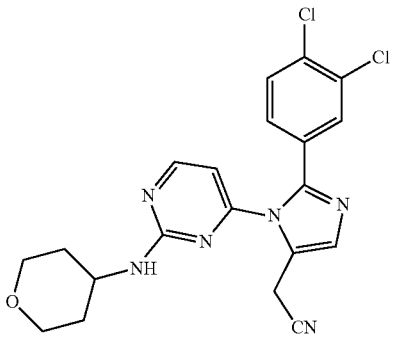 [SMILES: N#CCc1cnc(-c2ccc(Cl)c(Cl)c2)n1-c1ccnc(NC2CCOCC2)n1]

a white solid (89%); $^1$H NMR (400 MHz, DMSO) δ 8.41 (d, J=4.8 Hz, 1H), 7.73 (d, 1H), 7.68 (s, 1H), 7.54 (d, J=7.8 Hz, 1H), 7.35 (dd, J=8.4, 2.0 Hz, 1H), 6.77 (d, 1H), 4.00 (s, 2H), 3.83 (s, 1H), 3.77-3.67 (m, J=9.7 Hz, 2H), 3.12-2.93 (m, J=9.5 Hz, 3H), 1.38-1.24 (m, J=11.6 Hz, 4H); LRMS (ESI) m/z calcd for $C_{20}H_{18}Cl_2N_6O$ [M+H]+: 430, Found 430.

Example 6 Preparation of 2-(2-(4-fluoro-3-(trifluoromethyl)phenyl)-1-(2-(tetrahydro-2H-pyran-4-ylamino)pyrimidine-4-yl)-1H-imidazole-5-yl)acetonitrile (Compound 10f)

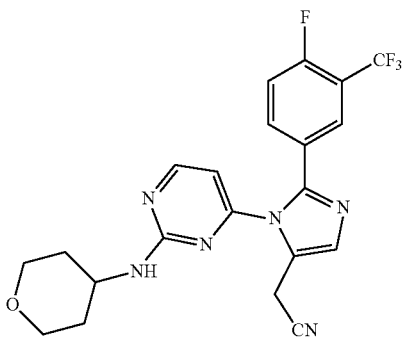 [SMILES: N#CCc1cnc(-c2ccc(F)c(C(F)(F)F)c2)n1-c1ccnc(NC2CCOCC2)n1]

a yellow solid (82%); $^1$H NMR (400 MHz, DMSO) δ 8.42 (d, 1H), 7.77 (d, J=5.1 Hz, 2H), 7.64-7.51 (m, J=22.3, 8.4 Hz, 2H), 6.77 (d, 1H), 4.01 (s, 2H), 3.71 (s, 1H), 3.03-2.93 (m, 2H), 2.10-2.06 (m, J=1.0 Hz, 2H), 1.58-1.42 (m, 1H), 1.37-1.22 (m, J=19.1, 13.5 Hz, 4H); LRMS (ESI) m/z calcd for $C_{21}H_{18}F_4N_6O$ [M+H]+: 447, Found 447.

Example 7 Preparation of 2-(2-(benzo[d][1,3]dioxol-5-yl)-1-(2-(cyclohexylamino)pyrimidine-4-yl)-1H-imidazole-5-yl)acetonitrile (Compound 11a)

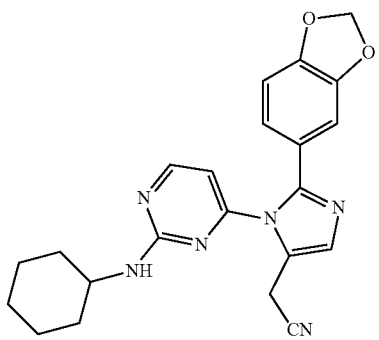 [SMILES: N#CCc1cnc(-c2ccc3c(c2)OCO3)n1-c1ccnc(NC2CCCCC2)n1]

The compound 9a (0.03 mmol) obtained in the Preparation Example 31 above and cyclohexyl amine (0.06 mmol) were stirred in THF (0.3 ml) at 60° C. for 5 hours. After the compound 9a completely disappeared, the reaction mixture was cooled down to room temperature, and concentrated under vacuum. The above concentrated mixture was separated and purified by means of a column chromatography (DCM:MEOH=40:1), so as to obtain a compound 11a.

a yellow solid (64%); $^1$H NMR (400 MHz, MeOD) δ 8.22 (s, 1H), 7.62 (s, 1H), 6.93-6.85 (m, J=14.0, 4.7 Hz, 3H), 6.47 (s, 1H), 6.00 (s, 2H), 3.87 (s, 2H), 3.55 (s, 1H), 1.79-1.65 (m, 3H), 1.65-1.58 (m, 1H), 1.36-1.26 (m, 2H), 1.26-1.05 (m, 5H); LRMS (ESI) m/z calcd for $C_{22}H_{22}N_6O_2$ [M+H]+: 403, Found 403.

Compounds of following Examples 8 to 12 were obtained by means of the same method as shown in the Example 7 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

Example 8 Preparation of 2-(1-(2-(cyclohexylamino)pyrimidine-4-yl)-2-(2,3-dihydrobenzo[b][1,4]dioxin-6-yl)-1H-imidazole-5-yl)acetonitrile (Compound 11b)

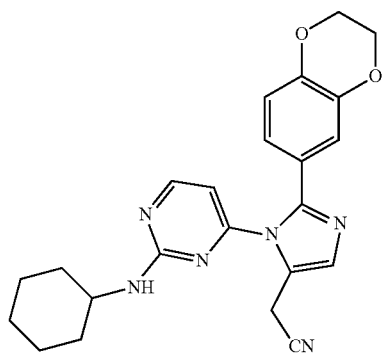 [SMILES: N#CCc1cnc(-c2ccc3c(c2)OCCO3)n1-c1ccnc(NC2CCCCC2)n1]

a white solid (25%); $^1$H NMR (400 MHz, DMSO) δ 8.33 (s, 1H), 7.57 (s, 1H), 7.41 (d, 1H), 6.87 (d, J=8.4 Hz, 1H), 6.83 (dd, J=8.4, 1.8 Hz, 1H), 6.34 (d, J=153.0 Hz, 1H), 4.29-4.19 (m, 4H), 3.95 (s, 2H), 3.18-3.05 (m, 1H), 1.90-1.68 (m, 1H), 1.65-1.49 (m, J=13.7 Hz, 4H), 1.27-1.21 (m, 2H), 1.13-0.99 (m, 4H); LRMS (ESI) m/z calcd for $C_{23}H_{24}N_6O_2$ [M+H]+: 417, Found 417.

Example 9 Preparation of 2-(1-(2-(cyclohexylamino)pyrimidine-4-yl)-2-(quinoline-2-yl)-1H-imidazole-5-yl)acetonitrile (Compound 11c)

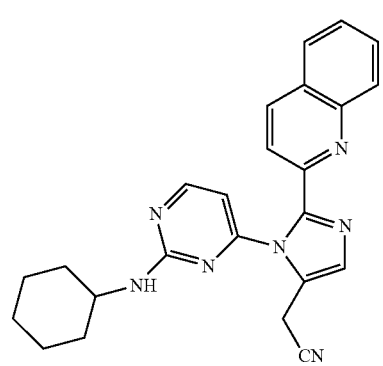 [SMILES: N#CCc1cnc(-c2ccc3ccccc3n2)n1-c1ccnc(NC2CCCCC2)n1]

a yellow solid (70%); $^1$H NMR (400 MHz, MeOD) δ 8.47-8.43 (m, J=8.5 Hz, 1H), 8.29 (d, J=4.5 Hz, 1H), 8.05 (d, J=6.0 Hz, 1H), 7.98 (d, J=8.1 Hz, 1H), 7.83-7.77 (m, 1H), 7.76 (s, 1H), 7.73 (d, J=7.2 Hz, 1H), 7.66-7.60 (m, J=11.5, 4.7 Hz, 1H), 6.54 (d, J=6.1 Hz, 1H), 3.97 (d, J=0.8 Hz, 2H), 2.04-1.98 (m, J=10.1 Hz, 2H), 1.82-1.75 (m, J=13.0 Hz, 2H), 1.70-1.64 (m, J=12.8 Hz, 1H), 1.46-1.43 (m, 1H), 1.43-1.40 (m, 1H), 1.40-1.37 (m, 1H), 1.27-1.25 (m, J=3.3 Hz, 1H), 1.24-1.22 (m, J=3.7 Hz, 1H); LRMS (ESI) m/z calcd for $C_{24}H_{23}N_7$ [M+H]+: 410, Found 410.

<Example 10> Preparation of 2-(1-(2-(cyclohexylamino)pyrimidine-4-yl)-2-(naphthalene-2-yl)-1H-imidazole-5-yl)acetonitrile (Compound 11d)

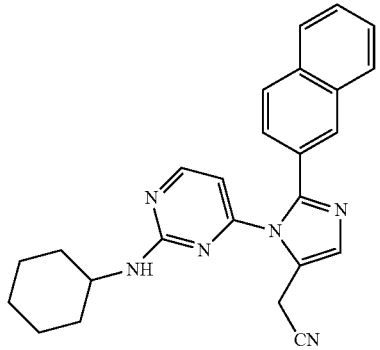 [SMILES: N#CCc1cnc(-c2ccc3ccccc3c2)n1-c1ccnc(NC2CCCCC2)n1]

a white solid (50%); ¹H NMR (400 MHz, CDCl₃) δ 8.06 (d, J=5.6 Hz, 1H), 8.03 (s, 1H), 7.84 (d, 1H), 7.81 (d, J=8.3 Hz, 2H), 7.63 (s, 1H), 7.55-7.47 (m, J=7.0, 3.5 Hz, 2H), 7.40 (d, J=8.3 Hz, 1H), 6.33 (d, J=83.7 Hz, 1H), 4.49 (s, 1H), 3.82 (s, 2H), 3.41-3.19 (m, 1H), 1.77-1.59 (m, 2H), 1.59-1.38 (m, J=42.8 Hz, 3H), 1.19-0.89 (m, 5H); LRMS (ESI) m/z calcd for $C_{25}H_{24}N_6$ [M+H]+: 409, Found 409.

<Example 11> Preparation of 2-(1-(2-(cyclohexylamino)pyrimidine-4-yl)-2-(3,4-dichlorophenphenyl)-1H-imidazole-5-yl)acetonitrile (Compound 11e)

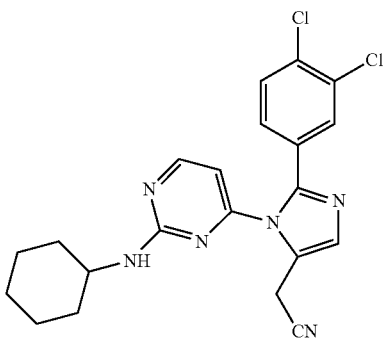 [SMILES: N#CCc1cnc(-c2ccc(Cl)c(Cl)c2)n1-c1ccnc(NC2CCCCC2)n1]

a white solid (58%); ¹H NMR (400 MHz, MeOD) δ 8.31 (d, J=5.2 Hz, 1H), 7.71 (s, 1H), 7.66 (d, J=1.4 Hz, 1H), 7.58 (d, J=8.3 Hz, 1H), 7.32 (dd, J=8.3, 2.0 Hz, 1H), 6.47 (d, J=89.7 Hz, 1H), 3.90 (s, 2H), 3.61 (s, 1H), 3.03-2.81 (m, J=39.3 Hz, 2H), 1.36-1.24 (m, 3H), 1.24-1.10 (m, 2H), 1.09-0.95 (m, 3H), 0.93-0.83 (m, 1H); LRMS (ESI) m/z calcd for $C_{21}H_{20}Cl_2N_6$ [M+H]+: 428, Found 428.

<Example 12> Preparation of 2-(1-(2-(cyclohexylamino)pyrimidine-4-yl)-2-(4-fluoro-3-(trifluoromethyl)phenyl)-1H-imidazole-5-yl)acetonitrile (Compound 11f)

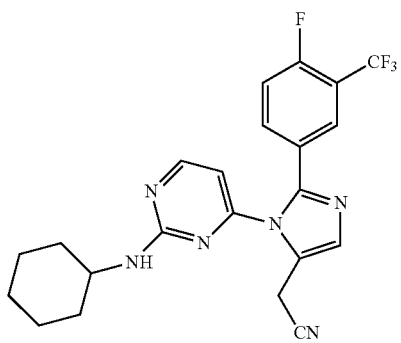 [SMILES: N#CCc1cnc(-c2ccc(F)c(C(F)(F)F)c2)n1-c1ccnc(NC2CCCCC2)n1]

a yellow solid (90%); ¹H NMR (400 MHz, DMSO) δ 8.39 (d, J=4.8 Hz, 1H), 7.77-7.73 (m, 2H), 7.58 (dd, J=9.8 Hz, 1H), 7.43 (d, J=7.8 Hz, 1H), 6.75 (d, J=4.4 Hz, 1H), 4.01 (s, 2H), 2.73 (s, 1H), 1.59-1.49 (m, 2H), 1.46-1.36 (m, J=12.3 Hz, 2H), 1.30-1.19 (m, J=20.4 Hz, 2H), 1.04-0.91 (m, J=22.7, 12.9 Hz, 3H), 0.91-0.82 (m, J=14.7, 7.3 Hz, 2H); LRMS (ESI) m/z calcd for $C_{22}H_{20}F_4N_6$ [M+H]+: 445, Found 445.

<Example 13> Preparation of 2-(2-(benzo[d][1,3]dioxol-5-yl)-1-(2-(2-hydroxypropylamino)pyrimidine-4-yl)-1H-imidazole-5-yl)acetonitrile (Compound 12a)

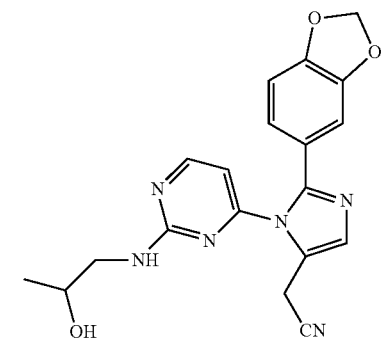 [SMILES: CC(O)CNc1nccc(-n2c(CC#N)cnc2-c2ccc3c(c2)OCO3)n1]

The compound 9a (0.03 mmol) obtained in the Preparation Example 31 above and 1-aminopropan-2-ol (0.06 mmol) were stirred in THF (0.3 ml) at 60° C. for 5 hours. After the compound 9a completely disappeared, the reaction mixture was cooled down to room temperature, and concentrated under vacuum. The above concentrated mixture was separated and purified by means of a column chromatography (DCM:MEOH=40:1), so as to obtain a compound 12a.

a yellow solid (61%); ¹H NMR (400 MHz, MeOD) δ 8.22 (d, J=5.2 Hz, 1H), 7.66 (d, J=0.7 Hz, 1H), 6.94-6.84 (m, J=15.4, 10.5, 4.8 Hz, 3H), 6.38 (s, 1H), 6.01 (s, 2H), 3.87 (s, 2H), 3.60 (s, 1H), 3.34 (s, 1H), 3.27-2.99 (m, 2H), 1.37-1.23 (m, 1H), 1.18-1.05 (m, 3H); LRMS (ESI) m/z calcd for $C_{19}H_{18}N_6O_3$ [M+H]+: 379, Found 379.

Compounds of following Examples 14 to 18 were obtained by means of the same method as shown in the Example 13 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Example 14> Preparation of 2-(2-(2,3-dihydrobenzo[b][1,4]dioxin-6-yl)-1-(2-(2-hydroxypropylamino)pyrimidine-4-yl)-1H-imidazole-5-yl)acetonitrile (Compound 12b)

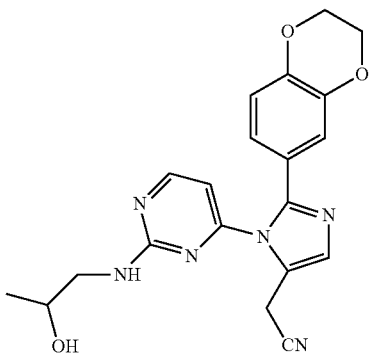 [SMILES: CC(O)CNc1nccc(-n2c(CC#N)cnc2-c2ccc3c(c2)OCCO3)n1]

a yellow solid (76%); $^1$H NMR (400 MHz, MeOD) δ 8.22 (d, J=5.3 Hz, 1H), 7.74-7.59 (m, 2H), 6.92 (s, 1H), 6.86 (d, J=1.2 Hz, 1H), 6.37 (d, 1H), 4.31-4.22 (m, J=5.4, 3.7, 1.7 Hz, 4H), 3.86 (d, J=0.9 Hz, 2H), 3.66 (s, 1H), 3.12 (s, 1H), 1.29-1.27 (m, 1H), 1.16-1.08 (m, 2H), 0.92-0.84 (m, 3H); LRMS (ESI) m/z calcd for $C_{20}H_{20}N_6O_3$ [M+H]+: 393, Found 393.

<Example 15> Preparation of 2-(1-(2-(2-hydroxypropylamino)pyrimidine-4-yl)-2-(quinoline-2-yl)-1H-imidazole-5-yl)acetonitrile (Compound 12c)

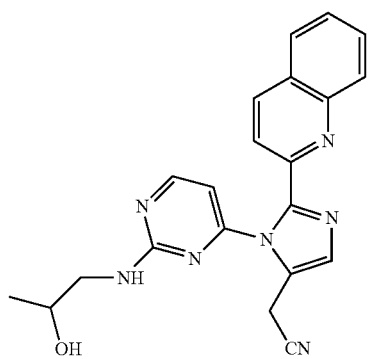 [SMILES: CC(O)CNc1nccc(-n2c(CC#N)cnc2-c2ccc3ccccc3n2)n1]

a white solid (38%); $^1$H NMR (400 MHz, MeOD) δ 8.44 (d, J=8.5 Hz, 1H), 8.28 (d, J=5.3 Hz, 1H), 7.97 (d, J=8.5 Hz, 2H), 7.80-7.69 (m, 3H), 7.66-7.59 (m, 1H), 6.61 (s, 1H), 4.26 (s, 27H), 3.97 (d, J=0.9 Hz, 52H), 2.65 (s, 8H), 2.06-1.96 (m, 1H), 1.35-1.24 (m, 2H), 0.93-0.65 (m, 3H); LRMS (ESI) calcd for $C_{21}H_{19}N_7O$[M+H]+: 386, Found 386.

<Example 16> Preparation of 2-(1-(2-(2-hydroxypropylamino)pyrimidine-4-yl)-2-(naphthalene-2-yl)-1H-imidazole-5-yl)acetonitrile (Compound 12d)

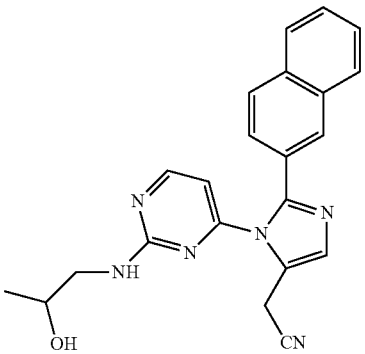 [SMILES: CC(O)CNc1nccc(-n2c(CC#N)cnc2-c2ccc3ccccc3c2)n1]

a white solid (85%); $^1$H NMR (400 MHz, CDCl$_3$) δ 8.04 (d, J=4.7 Hz, 1H), 8.01 (s, 1H), 7.82 (d, J=4.1 Hz, 1H), 7.80 (d, J=8.3 Hz, 2H), 7.64 (s, 1H), 7.54-7.46 (m, 2H), 7.40 (d, J=8.3 Hz, 1H), 6.14 (d, 1H), 3.93 (s, 1H), 3.80 (s, 2H), 3.21 (s, 1H), 1.30-1.18 (m, 3H), 0.99-0.91 (m, J=6.6, 3.1 Hz, 1H), 0.88-0.80 (m, 2H); LRMS (ESI) m/z calcd for $C_{22}H_{20}N_6O$ [M+H]+: 385, Found 385.

<Example 17> Preparation of 2-(2-(3,4-dichlorophenyl)-1-(2-(2-hydroxypropylamino)pyrimidine-4-yl)-1H-imidazole-5-yl)acetonitrile (Compound 12e)

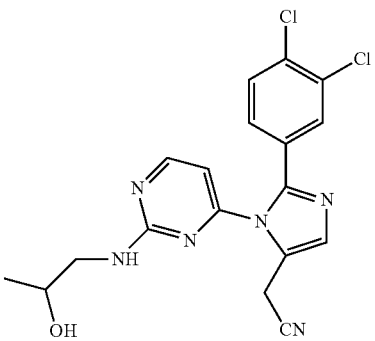 [SMILES: CC(O)CNc1nccc(-n2c(CC#N)cnc2-c2ccc(Cl)c(Cl)c2)n1]

a yellow solid (74%); $^1$H NMR (400 MHz, DMSO) δ 8.37 (d, J=5.1 Hz, 1H), 7.70-7.64 (m, 2H), 7.37-7.32 (m, 2H), 6.52 (d, J=83.1 Hz, 1H), 4.22 (d, J=13.3 Hz, 1H), 4.00 (s, 2H), 2.75 (s, 1H), 1.23 (s, 2H), 1.08-1.01 (m, 1H), 0.84 (d, J=4.0 Hz, 3H); LRMS (ESI) m/z calcd for $C_{18}H_{16}Cl_{12}N_6O$ [M+H]+: 404, Found 404.

Example 18> Preparation of 2-(2-(4-fluoro-3-(trifluoromethyl)phenyl)-1-(2-(2-hydroxypropylamino)pyrimidine-4-yl)-1H-imidazole-5-yl)acetonitrile (Compound 12f)

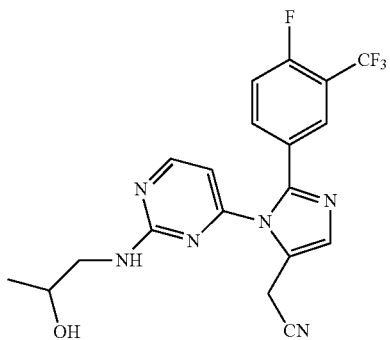 [SMILES: CC(O)CNc1nccc(-n2c(CC#N)cnc2-c2ccc(F)c(C(F)(F)F)c2)n1]

a white solid (78%); $^1$H NMR (400 MHz, DMSO) δ 8.37 (d, J=5.2 Hz, 1H), 7.79-7.73 (m, 2H), 7.61-7.51 (m, 1H), 7.36 (s, 1H), 6.60 (d, J=47.3, 36.1 Hz, 1H), 4.53 (s, 1H), 4.01 (s, 2H), 2.68 (s, 1H), 1.30-1.14 (m, 2H), 1.10-0.97 (m, 1H), 0.85 (dd, J=9.4, 4.7 Hz, 3H); LRMS (ESI) m/z calcd for $C_{19}H_{16}F_4N_6O$ [M+H]+: 421, Found 421.

Example 19> Preparation of tert-butyl 3-(4-(2-(benzo[d][1,3]dioxol-5-yl)-5-(cyanomethyl)-1H-imidazole-1-yl)pyrimidine-2-ylamino)piperidine-1-carboxylate (Compound 13a)

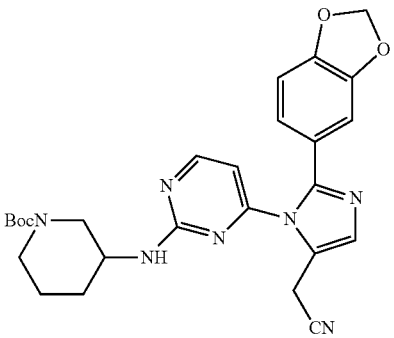 [SMILES: CC(C)(C)OC(=O)N1CCCC(Nc2nccc(-n3c(CC#N)cnc3-c3ccc4c(c3)OCO4)n2)C1]

The compound 9a (0.03 mmol) obtained in the Preparation Example 31 above and tert-butyl 3-aminopiperidine-1-carboxylate (0.06 mmol) were stirred in THF (0.3 ml) at 60° C. for 5 hours. After the compound 9a completely disappeared, the reaction mixture was cooled down to room temperature, and concentrated under vacuum. The above concentrated mixture was separated and purified by means of a column chromatography (DCM:MEOH=40:1), so as to obtain a compound 13a.

a yellow solid (89%); 1H NMR (400 MHz, MeOD) δ 8.23 (d, J=5.2 Hz, 1H), 7.74-7.59 (m, J=26.9, 4.4, 2.1 Hz, 1H), 6.93-6.84 (m, 3H), 6.31 (d, J=69.9 Hz, 1H), 6.02 (dd, J=3.5, 1.6 Hz, 2H), 4.03 (s, 1H), 3.86 (d, J=0.5 Hz, 2H), 3.70-3.52 (m, J=15.1 Hz, 1H), 3.52-3.36 (m, J=10.1, 9.3 Hz, 1H), 3.06-2.87 (m, J=2.3 Hz, 1H), 1.93-1.81 (m, 1H), 1.80-1.68 (m, 1H), 1.43 (s, 9H), 1.35-1.28 (m, 4H); LRMS (ESI) m/z calcd for $C_{26}H_{29}N_7O_4$ [M+H]+: 504, Found 504.

Compounds of following Examples 20 to 24 were obtained by means of the same method as shown in the Example 19 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

Example 20> Preparation of tert-butyl 3-(4-(5-(cyanomethyl)-2-(2,3-dihydrobenzo[b][1,4]dioxin-6-yl)-1H-imidazole-1-yl)pyrimidine-2-ylamino)piperidine-1-carboxylate (Compound 13b)

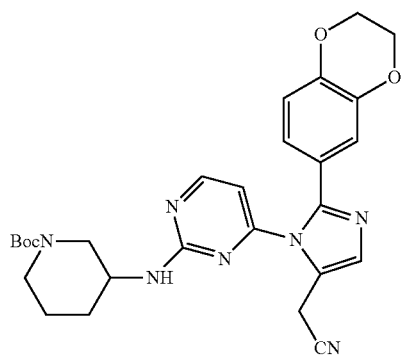 [SMILES: CC(C)(C)OC(=O)N1CCCC(Nc2nccc(-n3c(CC#N)cnc3-c3ccc4c(c3)OCCO4)n2)C1]

a yellow solid (53%); 1H NMR (400 MHz, MeOD) δ 8.24 (d, J=4.7 Hz, 1H), 7.74 (d, J=40.9 Hz, 1H), 6.94 (s, 1H), 6.91-6.84 (m, J=14.3 Hz, 2H), 6.29 (d, J=96.1 Hz, 1H), 4.30-4.26 (m, 2H), 4.26-4.23 (m, 2H), 3.88 (s, 2H), 3.80 (s, 1H), 3.10-2.91 (m, 1H), 1.91-1.80 (m, 1H), 1.80-1.69 (m, 1H), 1.43 (s, 9H), 1.38-1.24 (m, J=15.2 Hz, 6H); LRMS (ESI) m/z calcd for $C_{27}H_{31}N_7O_4$ [M+H]+: 518, Found 518.

Example 21> Preparation of tert-butyl 3-(4-(5-(cyanomethyl)-2-(quinoline-2-yl)-1H-imidazole-1-yl)pyrimidine-2-ylamino)piperidine-1-carboxylate (Compound 13c)

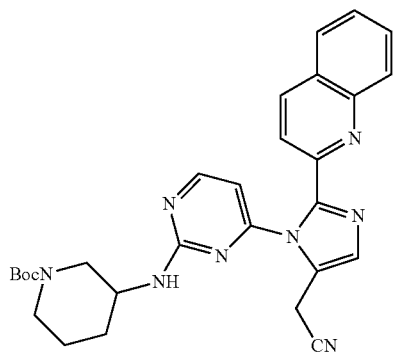 [SMILES: CC(C)(C)OC(=O)N1CCCC(Nc2nccc(-n3c(CC#N)cnc3-c3ccc4ccccc4n3)n2)C1]

a yellow solid (43%); $^1$H NMR (400 MHz, MeOD) δ 8.43 (d, J=8.5 Hz, 1H), 8.29 (d, J=4.5 Hz, 1H), 7.97 (d, J=8.0 Hz, 1H), 7.93-7.86 (m, 1H), 7.82-7.70 (m, J=13.3, 7.2 Hz, 2H), 7.62 (dd, J=11.0, 5.0 Hz, 1H), 6.65 (d, 1H), 3.97 (d, J=0.6 Hz, 2H), 3.59 (s, 1H), 2.95-2.64 (m, J=80.5 Hz, 2H), 1.48 (s, 8H), 1.34-1.18 (m, J=17.0 Hz, 4H), 1.12 (d, J=6.4 Hz, 1H), 1.01-0.81 (m, J=18.4, 12.0 Hz, 1H); LRMS (ESI) m/z calcd for $C_{28}H_{30}N_8O_2$ [M+H]+: 511, Found 511.

<Example 22> Preparation of tert-butyl 3-(4-(5-(cyanomethyl)-2-(naphthalene-2-yl)-1H-imidazole-1-yl)pyrimidine-2-ylamino)piperidine-1-carboxylate (Compound 13 d)

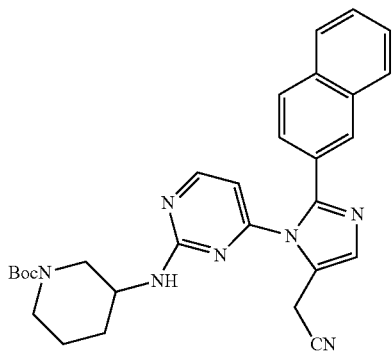 [SMILES: CC(C)(C)OC(=O)N1CCCC(Nc2nccc(-n3c(CC#N)cnc3-c3ccc4ccccc4c3)n2)C1]

a yellow solid (88%); $^1$H NMR (400 MHz, MeOD) δ 8.17 (s, 1H), 7.99 (s, 1H), 7.88-7.85 (m, 2H), 7.81 (dd, J=20.8 Hz, 2H), 7.56-7.49 (m, 2H), 7.39 (s, 1H), 6.47 (d, 1H), 3.91 (s, 2H), 3.79-3.56 (m, 1H), 3.55-3.33 (m, J=39.4 Hz, 1H), 3.03-2.67 (m, 2H), 2.02-1.97 (m, J=7.0, 3.3 Hz, 1H), 1.38 (s, 9H), 1.34-1.26 (m, 4H), 0.97-0.70 (m, 1H); LRMS (ESI) m/z calcd for $C_{29}H_{31}N_7O_2$ [M+H]+: 510, Found 510.

<Example 23> Preparation of tert-butyl 3-(4-(5-(cyanomethyl)-2-(3,4-dichlorophenyl)-1H-imidazole-1-yl)pyrimidine-2-ylamino)piperidine-1-carboxylate (Compound 13e)

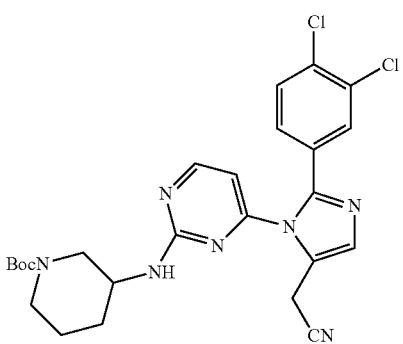 [SMILES: CC(C)(C)OC(=O)N1CCCC(Nc2nccc(-n3c(CC#N)cnc3-c3ccc(Cl)c(Cl)c3)n2)C1]

a yellow solid (83%); $^1$H NMR (400 MHz, MeOD) δ 8.33 (d, J=4.6 Hz, 1H), 7.71 (dd, J=5.4, 3.2 Hz, 1H), 7.66 (s, 1H), 7.56 (d, J=8.3 Hz, 1H), 7.32 (d, J=8.5 Hz, 1H), 6.62 (d, 1H), 3.90 (s, 2H), 3.73 (s, 1H), 3.10-2.82 (m, 2H), 2.65 (s, 1H), 1.76-1.66 (m, 2H), 1.28 (s, 9H), 0.92-0.82 (m, J=10.6, 5.9 Hz, 4H); LRMS (ESI) m/z calcd for $C_{25}H_{27}Cl_2N_4O_2$ [M+H]+: 528, Found 528.

<Example 24> Preparation of tert-butyl 3-(4-(5-(cyanomethyl)-2-(4-fluoro-3-(trifluoromethyl)phenyl)-1H-imidazole-1-yl)pyrimidine-2-ylamino)piperidine-1-carboxylate (Compound 13f)

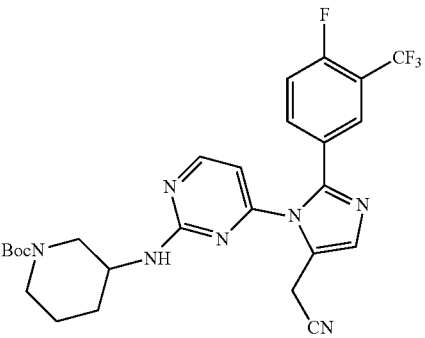 [SMILES: CC(C)(C)OC(=O)N1CCCC(Nc2nccc(-n3c(CC#N)cnc3-c3ccc(F)c(C(F)(F)F)c3)n2)C1]

a yellow solid (58%); $^1$H NMR (400 MHz, DMSO) δ 8.43-8.37 (m, J=5.2 Hz, 1H), 7.77 (d, J=5.8 Hz, 1H), 7.71 (d, J=5.9 Hz, 1H), 7.55 (s, 2H), 6.68 (d, J=4.3 Hz, 1H), 4.01 (s, 2H), 3.82-3.69 (m, 1H), 3.68-3.56 (m, J=21.6, 14.3 Hz, 1H), 3.37 (s, 1H), 2.94-2.80 (m, J=4.2 Hz, 1H), 2.79-2.65 (m, 1H), 2.23-2.11 (m, 1H), 1.55-1.45 (m, 2H), 1.37 (s, 8H), 1.24-1.20 (m, 2H); LRMS (ESI) m/z calcd for $C_{26}H_{27}F_4N_7O_2$ [M+H]+: 546, Found 546.

<Example 25> Preparation of 2-(2-(benzo[d][1,3]dioxol-5-yl)-1-(2-(piperidine-3-ylamino)pyrimidine-4-yl)-1H-imidazole-5-yl) acetonitrile (Compound 14a)

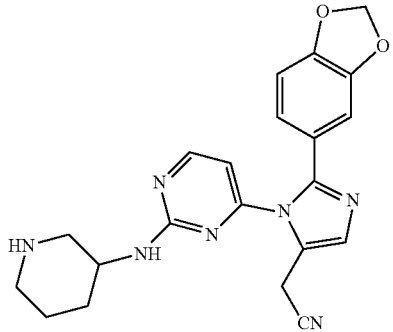 [SMILES: N#CCc1cnc(-c2ccc3c(c2)OCO3)n1-c1ccnc(NC2CCCNC2)n1]

The compound 13a (18 mg, 0.033 mmol) obtained in the Example 19 above was dissolved in 1,4-dioxane (0.33 ml), and treated in 1,4-dioxane by means of 4 M-HCl (0.17 ml), and then the above reaction mixture was stirred at room temperature for 20 minutes. The above mixture was diluted with an addition of ether, and stirred until a solid product was separated therefrom. The above solid product was filtered, sequentially washed with ether and hexane solvents, and crystalized, so as to obtain a compound 14a.

a white solid (61%); $^1$H NMR (400 MHz, MeOD) δ 8.28 (d, J=5.3 Hz, 1H), 7.70 (s, 1H), 6.94-6.85 (m, 3H), 6.38 (d, J=12.5 Hz, 1H), 6.02 (s, 2H), 4.04 (s, 1H), 3.88 (d, J=0.8 Hz, 2H), 3.53-3.35 (m, 1H), 3.35-3.31 (m, 1H), 3.29-3.24 (m, 1H), 3.01-2.80 (m, 2H), 2.12-1.92 (m, J=15.5, 12.9 Hz, 2H), 1.82-1.71 (m, J=7.8 Hz, 1H), 1.69-1.57 (m, 1H), 1.40-0.93 (m, 1H); LRMS (ESI) m/z calcd for $C_{21}H_{21}N_7O_2$ [M+H]+: 404, Found 404.

Compounds of following Examples 26 to 30 were obtained by means of the same method as shown in the Example 25 above (1,3-benzodioxolyl was substituted with 2,3-dihydro-1,4 benzodioxinyl, quinolinyl, naphthylyl, 3,4-dichlorophenyl and 4-fluoro-3-(trifluoromethyl)phenyl, respectively).

<Example 26> Preparation of 2-(2-(2,3-dihydrobenzo[b][1,4]dioxin-6-yl)-1-(2-(piperidine-3-ylamino)pyrimidine-4-yl)-1H-imidazole-5-yl)acetonitrile (Compound 14b)

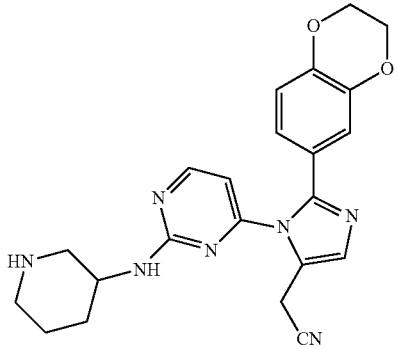 [SMILES: N#CCc1cnc(-c2ccc3c(c2)OCCO3)n1-c1ccnc(NC2CCCNC2)n1]

a white solid (91%); $^1$H NMR (400 MHz, MeOD) δ 8.41-8.37 (m, J=4.3 Hz, 1H), 8.01 (d, J=39.3 Hz, 1H), 7.05 (d, J=14.0 Hz, 1H), 7.01-6.97 (m, J=4.9 Hz, 2H), 6.56 (d, J=65.3 Hz, 1H), 4.35-4.31 (m, J=3.6, 1.7 Hz, 2H), 4.31-4.27 (m, J=3.5, 1.6 Hz, 2H), 4.12 (s, 1H), 4.09 (d, J=0.8 Hz, 2H), 3.60-3.57 (m, 1H), 3.47-3.37 (m, J=25.5 Hz, 1H), 3.35-3.32 (m, 1H), 2.94 (m, J=26.5, 11.4 Hz, 2H), 2.08-1.99 (m, 1H), 1.92-1.75 (m, 2H), 1.65 (s, 2H); LRMS (ESI) m/z calcd for $C_{22}H_{23}N_7O_2$ [M+H]+: 418, Found 418.

<Example 27> Preparation of 2-(1-(2-(piperidine-3-ylamino)pyrimidine-4-yl)-2-(quinoline-2-yl)-1H-imidazole-5-yl)acetonitrile (Compound 14c)

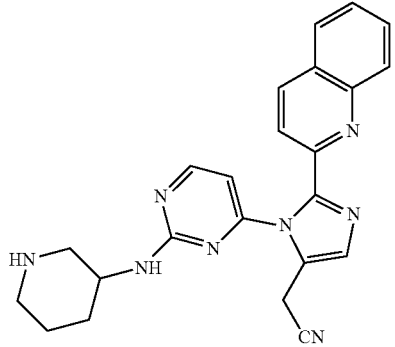 [SMILES: N#CCc1cnc(-c2ccc3ccccc3c2)n1-c1ccnc(NC2CCCNC2)n1]

a yellow solid (47%); $^1$H NMR (400 MHz, MeOD) δ 8.45 (d, J=8.5 Hz, 1H), 8.34 (d, J=5.3 Hz, 1H), 8.01 (d, J=8.5 Hz, 1H), 7.97 (d, J=8.1 Hz, 1H), 7.76 (s, 1H), 7.75-7.70 (m, 1H), 7.67 (d, J=7.7 Hz, 1H), 7.64-7.59 (m, J=8.1, 6.6, 1.5 Hz, 1H), 6.59 (s, 1H), 3.97 (d, J=0.8 Hz, 2H), 3.18-3.07 (m, 1H), 2.83 (s, 1H), 2.67 (s, 1H), 2.08-1.96 (m, J=9.6 Hz, 1H), 1.87-1.65 (m, J=10.8 Hz, 2H), 1.60-1.41 (m, J=28.7 Hz, 2H), 1.35-1.22 (m, 2H), 0.99-0.80 (m, J=18.1, 12.1 Hz, 1H); LRMS (ESI) m/z calcd for $C_{23}H_{22}N_8$ [M+H]+: 411, Found 411.

<Example 28> Preparation of 2-(2-(naphthalene-2-yl)-1-(2-(piperidine-3-ylamino)pyrimidine-4-yl)-1H-imidazole-5-yl)acetonitrile (Compound 14d)

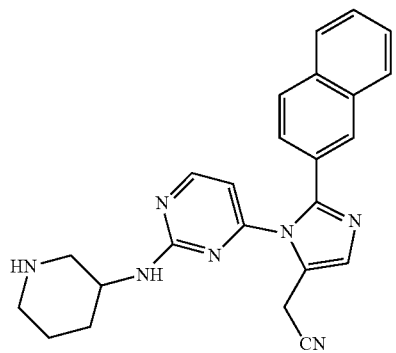

a white solid (89%); $^1$H NMR (400 MHz, MeOD) δ 8.15 (s, 1H), 7.92 (s, 1H), 7.88-7.77 (m, 4H), 7.52-7.44 (m, 2H), 7.36 (d, J=8.3 Hz, 1H), 6.20 (d, J=93.0 Hz, 1H), 3.91 (s, 2H), 3.62 (s, 1H), 3.21-3.05 (m, 2H), 2.90-2.73 (m, 2H), 2.05-1.90 (m, J=25.3 Hz, 1H), 1.83-1.56 (m, 2H), 1.52-1.25 (m, 3H); LRMS (ESI) m/z calcd for $C_{24}H_{23}N_7$ [M+H]+: 418, Found 418.

<Example 29> Preparation of 2-(2-(3,4-dichlorophenyl)-1-(2-(piperidine-3-ylamino)pyrimidine-4-yl)-1H-imidazole-5-yl)acetonitrile (Compound 14e)

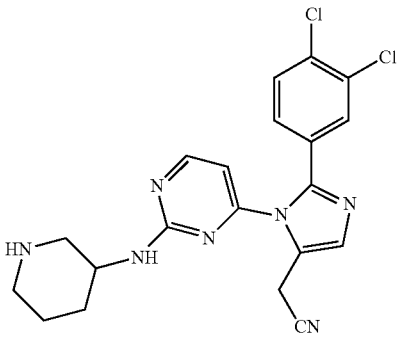 [SMILES: N#CCc1cnc(-c2ccc(Cl)c(Cl)c2)n1-c1ccnc(NC2CCCNC2)n1]

a white solid (47%); $^1$H NMR (400 MHz, MeOD) δ 8.45 (d, J=5.5 Hz, 1H), 8.10 (s, 1H), 7.83 (d, J=1.5 Hz, 1H), 7.73 (d, J=8.3 Hz, 1H), 7.50 (dd, J=8.6 Hz, 1H), 6.66 (d, 1H), 4.13 (s, 2H), 3.95 (s, 1H), 3.81-3.62 (m, 1H), 3.61-3.56 (m, 1H), 3.02-2.86 (m, 3H), 2.03 (s, 1H), 1.89-1.73 (m, 2H), 1.71-1.55 (m, J=37.0 Hz, 2H). LRMS (ESI) m/z calcd for $C_{20}H_{19}Cl_2N_7$ [M+H]+: 429, Found 429.

\<Example 30\> Preparation of 2-(2-(4-fluoro-3-(trifluoromethyl)phenyl)-1-(2-(piperidine-3-ylamino)pyrimidine-4-yl)-1H-imidazole-5-yl)acetonitrile (Compound 14f)

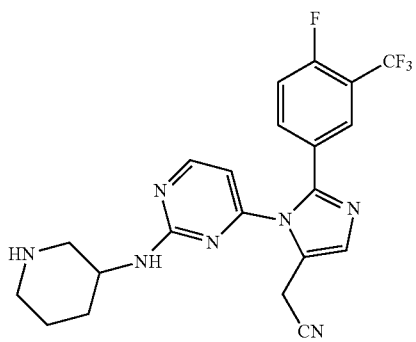 [SMILES: N#CCc1cnc(-c2ccc(F)c(C(F)(F)F)c2)n1-c1ccnc(NC2CCCNC2)n1]

a white solid (67%); $^1$H NMR (400 MHz, DMSO) δ 8.38 (d, 1H), 7.74 (s, 2H), 7.56 (d, J=8.9 Hz, 1H), 7.42 (d, 1H), 6.67 (d, J=4.4 Hz, 1H), 4.01 (s, 2H), 3.76 (s, 1H), 3.45-3.35 (m, J=5.6 Hz, 1H), 3.05-2.91 (m, 1H), 2.72-2.59 (m, 1H), 2.42-2.13 (m, 2H), 1.51-1.33 (m, 2H), 1.35-1.20 (m, J=32.9, 17.3 Hz, 2H), 0.88-0.80 (m, 1H); LRMS (ESI) m/z calcd for $C_{21}H_{19}F_4N_7$ [M+H]+: 446, Found 446.

\<Example 31\> Preparation of 2-(2-(benzo[d][1,3]dioxol-5-yl)-1-(2-(1-(cyclopropanecarbonyl)piperidine-3-ylamino)pyrimidine-4-yl)-1H-imidazole-5-yl)acetonitrile (Compound 15a)

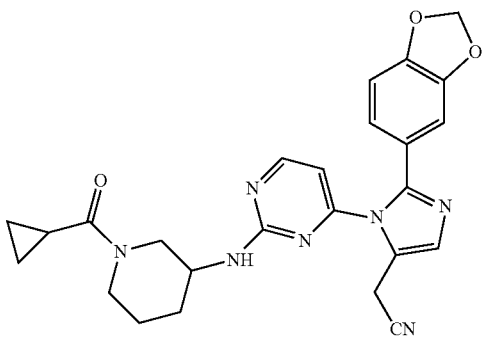 [SMILES: N#CCc1cnc(-c2ccc3c(c2)OCO3)n1-c1ccnc(NC2CCCN(C(=O)C3CC3)C2)n1]

The compound 14a (10 mg, 0.024 mmol) obtained in the Example 25 above was cooled down to 0° C. in THF (0.24 ml), and treated with TEA (5 μL, 0.038 mmol). Cyclopropanecarbonyl chloride (6.5 mg, 0.024 mmol) was added into the above mixture at 0° C., and stirred at room temperature for 1 hour. After the above reaction mixture was concentrated under vacuum, a resulting concentrate was diluted with methylene chloride, and washed with water and saturated sodium chloride aqueous solution. An organic layer was dehydrated with sodium sulfate, and then a resulting residue was concentrated under vacuum, and separated and purified by means of a column chromatography (DCM:MEOH=40:1), so as to obtain a compound 15a.

a white solid (49%); $^1$H NMR (400 MHz, MeOD) δ 8.33-8.16 (m, 1H), 7.69 (d, J=40.8 Hz, 1H), 6.90 (dd, J=7.9, 1.7 Hz, 1H), 6.89-6.84 (m, J=7.0 Hz, 2H), 6.44 (d, J=44.0 Hz, 1H), 6.01 (d, J=5.7 Hz, 2H), 4.11 (d, J=12.8 Hz, 1H), 3.87 (d, J=0.8 Hz, 2H), 3.49-3.33 (m, 1H), 3.09-2.70 (m, J=116.5 Hz, 1H), 2.07-1.63 (m, J=75.2, 39.4, 22.7 Hz, 4H), 1.62-1.45 (m, 2H), 1.34-1.20 (m, 1H), 0.97-0.73 (m, 4H), 0.72-0.55 (m, J=32.5, 25.1 Hz, 1H); LRMS (ESI) m/z calcd for $C_{25}H_{25}N_7O_3$ [M+H]+: 472, Found 472.

Compounds of following Examples 32 to 37 were obtained by means of the same method as shown in the Example 31 above (1,3-benzodioxolyl was substituted with 2,3-dihydro-1,4 benzodioxinyl, quinolinyl, naphthylyl, 3,4-dichlorophenyl, 4-fluoro-3-(trifluoromethyl)phenyl and benzofuranyl, respectively).

\<Example 32\> Preparation of 2-(1-(2-(1-(cyclopropanecarbonyl)piperidine-3-ylamino)pyrimidine-4-yl)-2-(2,3-dihydrobenzo[b][1,4]dioxin-6-yl)-1H-imidazole-5-yl)acetonitrile (Compound 15b)

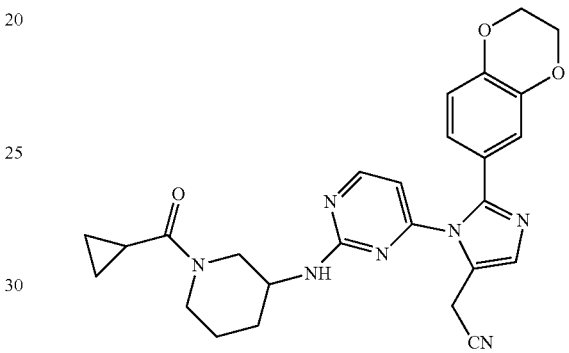

a white solid (82%); $^1$H NMR (400 MHz, MeOD) δ 8.24 (d, 1H), 7.72 (d, J=5.7, 3.1 Hz, 1H), 7.61 (d, 1H), 6.93-6.83 (m, 2H), 6.45 (d, J=53.2 Hz, 1H), 4.31-4.21 (m, 4H), 3.96 (s, 1H), 3.87 (s, 2H), 3.08-2.94 (m, 1H), 2.06-1.86 (m, 2H), 1.79-1.67 (m, 2H), 1.64-1.52 (m, 2H), 1.38-1.33 (m, J=18.1 Hz, 2H), 0.92-0.85 (m, J=7.4, 6.0, 4.0 Hz, 5H); LRMS (ESI) m/z calcd for $C_{26}H_{27}N_7O_3$ [M+H]+: 486, Found 486.

\<Example 33\> Preparation of 2-(1-(2-(1-(cyclopropanecarbonyl)piperidine-3-ylamino)pyrimidine-4-yl)-2-(quinoline-2-yl)-1H-imidazole-5-yl)acetonitrile (Compound 15c)

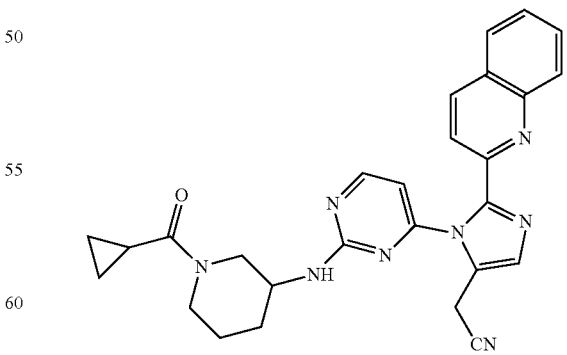

a yellow solid (32%); $^1$H NMR (400 MHz, MeOD) δ 8.44-8.40 (m, J=8.5 Hz, 1H), 8.30 (dd, 1H), 8.02-7.94 (m, J=8.6 Hz, 2H), 7.87 (d, J=23.8 Hz, 1H), 7.75 (s, 1H), 7.73-7.67 (m, 1H), 7.66-7.58 (m, 1H), 6.69 (d, 1H), 3.97 (d, J=0.7 Hz, 2H), 3.89 (s, 1H), 2.95-2.70 (m, 2H), 2.06-1.99 (m, J=9.8 Hz, 1H), 1.97-1.87 (m, 1H), 1.57-1.46 (m, 2H), 1.32-1.26 (m, 2H), 1.00-0.92 (m, 1H), 0.91-0.77 (m, J=20.3, 6.7 Hz, 3H), 0.67-0.42 (m, 2H); LRMS (ESI) m/z calcd for $C_{27}H_{26}N_8O$ [M+H]+: 479, Found 479.

<Example 34> Preparation of 2-(1-(2-(1-(cyclopropanecarbonyl)piperidine-3-ylamino)pyrimidine-4-yl)-2-(naphthalene-2-yl)-1H-imidazole-5-yl)acetonitrile (Compound 15d)

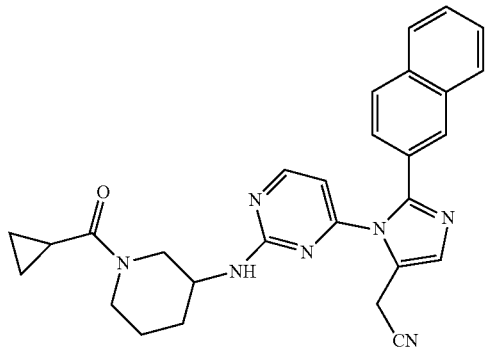 [SMILES: N#CCc1cnc(-c2ccc3ccccc3c2)n1-c1ccnc(NC2CCCN(C(=O)C3CC3)C2)n1]

a yellow solid (43%); $^1$H NMR (400 MHz, MeOD) δ 8.23 (d, J=42.0 Hz, 1H), 7.99 (d, J=5.5 Hz, 1H), 7.92-7.81 (m, J=11.6, 8.5 Hz, 3H), 7.71 (s, 1H), 7.56-7.48 (m, 2H), 7.37 (d, J=7.2 Hz, 1H), 6.53 (d, J=56.5 Hz, 1H), 3.91 (s, 2H), 3.86 (s, 1H), 2.92-2.68 (m, J=29.7, 20.7 Hz, 2H), 1.88-1.81 (m, J=7.3, 2.8 Hz, 1H), 1.64-1.50 (m, 2H), 0.98-0.83 (m, 4H), 0.82-0.64 (m, 4H), 0.61-0.51 (m, J=8.2 Hz, 1H); LRMS (ESI) m/z calcd for $C_{28}H_{27}N_7O$ [M+H]+: 478, Found 478.

<Example 35> Preparation of 2-(1-(2-(1-(cyclopropanecarbonyl)piperidine-3-ylamino)pyrimidine-4-yl)-2-(3,4-dichlorophenyl)-1H-imidazole-5-yl)acetonitrile (Compound 15e)

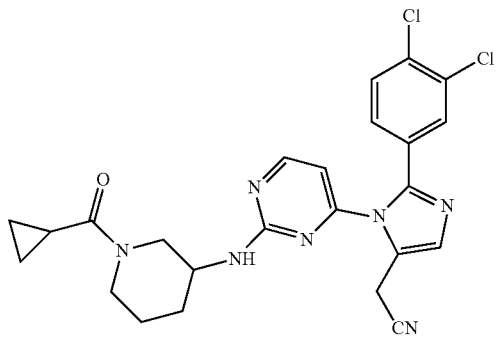 [SMILES: N#CCc1cnc(-c2ccc(Cl)c(Cl)c2)n1-c1ccnc(NC2CCCN(C(=O)C3CC3)C2)n1]

a white solid (32%); $^1$H NMR (400 MHz, MeOD) δ 8.33 (d, 1H), 7.73 (d, J=24.2 Hz, 1H), 7.65 (s, 1H), 7.56 (dd, J=8.2, 5.3 Hz, 1H), 7.32 (d, J=8.0 Hz, 1H), 6.68 (d, 1H), 4.28 (s, 1H), 3.90 (d, J=0.8 Hz, 2H), 2.68-2.51 (m, 2H), 2.06-1.97 (m, 2H), 1.87-1.73 (m, 2H), 1.59-1.47 (m, 2H), 1.31-1.25 (m, 2H), 0.94-0.76 (m, 4H), 0.68-0.58 (m, 1H); LRMS (ESI) m/z calcd for $C_{24}H_{23}Cl_2N_7O$ [M+H]+: 497, Found 497.

<Example 36> Preparation of 2-(1-(2-(1-(cyclopropanecarbonyl)piperidine-3-ylamino)pyrimidine-4-yl)-2-(4-fluoro-3-(trifluoro methyl)phenyl)-1H-imidazole-5-yl)acetonitrile (Compound 15f)

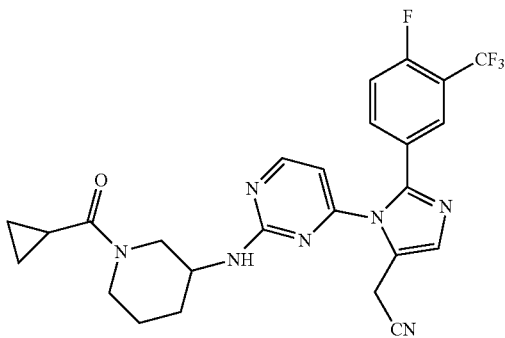 [SMILES: N#CCc1cnc(-c2ccc(F)c(C(F)(F)F)c2)n1-c1ccnc(NC2CCCN(C(=O)C3CC3)C2)n1]

a white solid (35%); $^1$H NMR (400 MHz, MeOD) δ 8.32 (d, J=4.8 Hz, 1H), 7.79 (d, 1H), 7.71 (s, 1H), 7.39 (d, J=8.2 Hz, 1H), 6.62 (d, 1H), 4.21 (s, 1H), 3.91 (d, J=0.8 Hz, 2H), 3.08-2.99 (m, 1H), 1.85-1.75 (m, 4H), 1.57-1.50 (m, 4H), 0.91-0.85 (m, J=7.0, 4.6 Hz, 5H); LRMS (ESI) m/z calcd for $C_{25}H_{23}F_4N_7O$ [M+H]+: 514, Found 514.

<Example 37> Preparation of 2-(2-(benzofuran-5-yl)-1-(2-(1-cyclopropanecarbonyl)piperidine-3-ylamino)pyrimidine-4-yl)-1H-imidazole-5-yl)acetonitrile (Compound 15g)

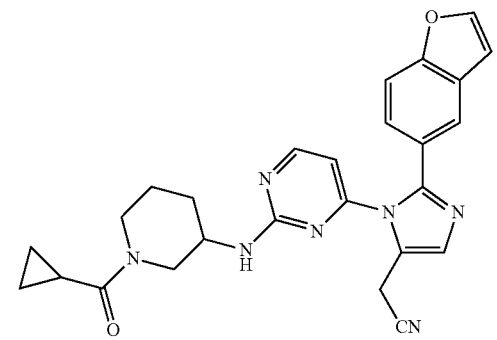 [SMILES: N#CCc1cnc(-c2ccc3occc3c2)n1-c1ccnc(NC2CCCN(C(=O)C3CC3)C2)n1]

$^1$H NMR (400 MHz, DMSO) δ 8.30 (d, J=22.8 Hz, 1H), 8.03 (s, 1H), 7.93 (m, 1H), 7.72 (d, J=10.2 Hz, 1H), 7.65 (s, 1H), 7.49-7.37 (m, 1H), 6.82 (d, J=7.4 Hz, 1H), 6.58-6.11 (m, 1H), 4.10 (s, NH, 1H), 3.81 (s, 2H), 3.38 (s, 2H), 2.87 (s, 1H), 1.81 (m, 2H), 1.65-1.45 (m, 2H), 1.34 (m, 2H), 0.76-0.58 (m, 5H). LRMS (ESI) m/z calcd for $C_{26}H_{25}N_7O_2$ [M+H]+: 467, Found 467.

Experimental Example 1: Measurement of JNK3 Enzyme Activity

The changes in JNK3 enzyme activity resulting from being treated with the inventive imidazole derivative (Formula 1) shown in a following Table 1 were identified through $IC_{50}$.

TABLE 1

| Example | Compound No. | R₁ | R₂ |
|---|---|---|---|
| 1 | 10a | benzo[1,3]dioxole | tetrahydro-2H-pyran-4-yl |
| 2 | 10b | 2,3-dihydro-1,4-benzodioxine | tetrahydro-2H-pyran-4-yl |
| 3 | 10c | quinolin-2-yl | tetrahydro-2H-pyran-4-yl |
| 4 | 10d | naphthalen-2-yl | tetrahydro-2H-pyran-4-yl |
| 5 | 10e | 3,4-dichlorophenyl | tetrahydro-2H-pyran-4-yl |
| 6 | 10f | 4-fluoro-3-(trifluoromethyl)phenyl | tetrahydro-2H-pyran-4-yl |
| 7 | 11a | benzo[1,3]dioxole | cyclohexyl |
| 8 | 11b | 2,3-dihydro-1,4-benzodioxine | cyclohexyl |
| 9 | 11c | quinolin-2-yl | cyclohexyl |
| 10 | 11d | naphthalen-2-yl | cyclohexyl |
| 11 | 11e | 3,4-dichlorophenyl | cyclohexyl |
| 12 | 11f | 4-fluoro-3-(trifluoromethyl)phenyl | cyclohexyl |
| 13 | 12a | benzo[1,3]dioxole | (R)-2-hydroxypropyl |

TABLE 1-continued
| Example | Compound No. | R₁ | R₂ |
|---------|--------------|-----|-----|
| 14 | 12b | 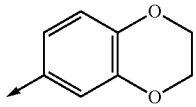 | 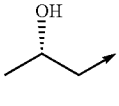 |
| 15 | 12c | 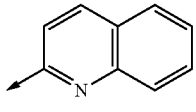 | 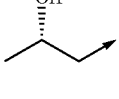 |
| 16 | 12d | 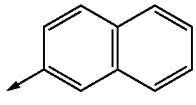 | 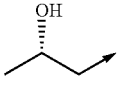 |
| 17 | 12e | 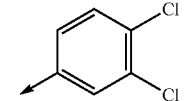 | 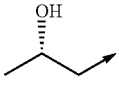 |
| 18 | 12f | 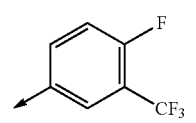 | 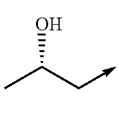 |
| 25 | 14a | 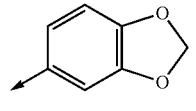 | 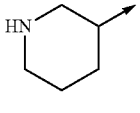 |
| 26 | 14b | 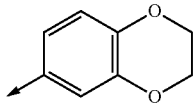 | 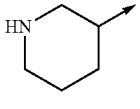 |
| 27 | 14c | 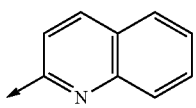 | 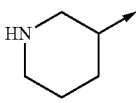 |
| 28 | 14d | 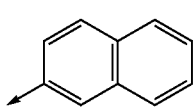 | 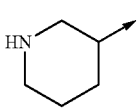 |
| 29 | 14e | 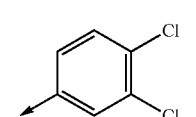 | 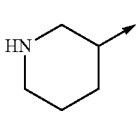 |
| 30 | 14f | 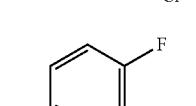 | 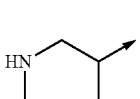 |
| 31 | 15a | 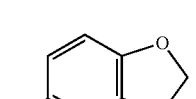 | 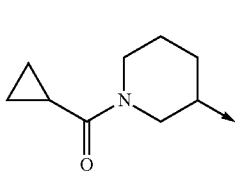 |

TABLE 1-continued

| Example | Compound No. | R₁ | R₂ |
|---|---|---|---|
| 32 | 15b | 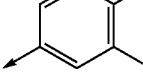 |  |
| 33 | 15c | 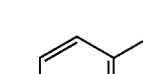 |  |
| 34 | 15d | 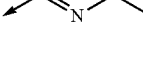 | 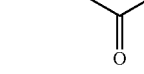 |
| 35 | 15e | 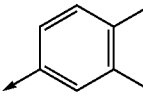 |  |
| 36 | 15f | 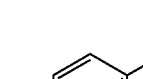 |  |
| 37 | 15g | 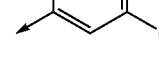 | 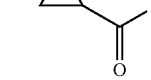 |

First of all, after a substrate was inserted into a prepared base reaction buffer solution (20 mM Hepes (pH 75), 10 mM MgCl$_2$, 1 mM EGTA, 0.02% Brij35, 0.02 mg/ml BSA, 0.1 mM Na$_3$VO$_4$, 2 mM DTT, 1% DMSO), a human JNK3 enzyme was added into a prepared substrate solution and then mixed together. As the substrate, ATP (10 μM) and ATF2 (3 μM) were used, among which the ATP was also used as a common substrate. Then, compounds of Examples 1-18 and 25-36, which were dissolved in 100% DMSO, were inserted into an enzyme reaction solution, and then cultured at room temperature for 20 minutes. Then, $^{33}$P-ATP was inserted into the above reaction mixture solution to initiate a reaction, then cultured at room temperature for 2 hours, and then an enzyme activity was detected by means of a filter-binding method.

Particularly, after each 25 μl of the resulting solution was slowly spotted on P81 paper, it was inserted into a scintillation vial, and washed with 0.75% phosphoric acid four times for 10 minutes each, and with acetone once for 5 minutes. 5 ml of scintillation cocktail was inserted into the above scintillation vial and a resulting signal was read by means of a scintillation counter.

IC$_{50}$ values of compounds of Examples 1-18 and 25-36 with regard to JNK3 enzyme activity were shown in a following Table 2. The results showed that the imidazole derivative according to the present invention had an excellent inhibitory activity against JNK3.

TABLE 2

| Example | Compound No. | JNK3 (IC$_{50}$) |
|---|---|---|
| 1 | 10a | ++ |
| 2 | 10b | + |
| 3 | 10c | ++ |
| 4 | 10d | +++ |
| 5 | 10e | ++ |
| 6 | 10f | ++ |
| 7 | 11a | + |
| 8 | 11b | + |
| 9 | 11c | + |
| 10 | 11d | ++ |
| 11 | 11e | ++ |
| 12 | 11f | + |
| 13 | 12a | ++ |
| 14 | 12b | ++ |
| 15 | 12c | ++ |
| 16 | 12d | ++ |
| 17 | 12e | ++ |
| 18 | 12f | ++ |
| 25 | 14a | + |

TABLE 2-continued

| Example | Compound No. | JNK3 (IC$_{50}$) |
|---|---|---|
| 26 | 14b | ++ |
| 27 | 14c | ++ |
| 28 | 14d | +++ |
| 29 | 14e | ++ |
| 30 | 14f | ++ |
| 31 | 15a | ++ |
| 32 | 15b | ++ |
| 33 | 15c | +++ |
| 34 | 15d | +++ |
| 35 | 15e | ++ |
| 36 | 15f | ++ |
| 37 | 15g | +++ |

+: IC$_{50}$ value of >100 nM
++: IC$_{50}$ value of 30-100 nM
+++: IC$_{50}$ value of <30 nM Experimental Example 2: Measurement of Inhibitory Activity Against Various Protein Kinases An inhibitory activity of the compound (10 μM) of Example 34 against various protein kinases was measured by means of a kinase profiling service (ICso profiler express) of Reaction Biology Corp., wherein ICso, a concentration at which JNK enzyme activity was inhibited 50%, was also measured by sequentially reducing a concentration of the compound.

IC$_{50}$ values of the compound of Example 34 with regard to various protein kinases were shown in a following Table 3. The results showed that the imidazole derivative according to the present invention had an excellent inhibitory activity against JNK1/2/3, but did not had an inhibitory activity against other protein kinases, thus it may be seen that such imidazole derivative was capable of selectively inhibiting the activity of JNK1/2/3.

TABLE 3

| | % Enzyme Activity (relative to DMSO controls) Compound of Example 34 | |
|---|---|---|
| Protein Kinases | Data 1 | Data 2 |
| ABL1 | 95.29 | 94.12 |
| AKT1 | 102.55 | 99.04 |
| ALK | 97.99 | 97.85 |
| Aurora A | 102.07 | 101.98 |
| c-Kit | 93.41 | 92.65 |
| c-MET | 105.01 | 90.72 |
| c-Src | 94.04 | 92.54 |
| CDK1/cyclin B | 90.68 | 90.33 |
| CDK2/cyclin E | 97.45 | 95.83 |
| EGFR | 68.38 | 67.11 |
| ERK1 | 98.55 | 97.98 |
| ERK2/MAPK1 | 97.99 | 97.70 |
| FAK/PTK2 | 101.14 | 99.94 |
| FGFR3 | 91.43 | 91.29 |
| FLT3 | 98.70 | 96.52 |
| FMS | 93.70 | 93.11 |
| FYN | 95.56 | 94.86 |
| GSK3b | 29.90 | 29.80 |
| IGF1R | 93.11 | 92.45 |
| JAK3 | 101.17 | 99.82 |
| JNK1 | 3.04 | 2.84 |
| JNK2 | 1.41 | 1.40 |
| JNK3 | 5.04 | 4.81 |
| KDR/VEGFR2 | 74.06 | 73.81 |
| LCK | 95.79 | 95.50 |
| LRRK2 | 96.33 | 95.95 |
| LYN | 86.61 | 85.66 |

TABLE 3-continued

| | % Enzyme Activity (relative to DMSO controls) Compound of Example 34 | |
|---|---|---|
| Protein Kinases | Data 1 | Data 2 |
| MEK1 | 104.88 | 104.84 |
| MLK1/MAP3K9 | 95.65 | 93.90 |
| mTOR/FRAP1 | 104.62 | 101.65 |
| PKA | 97.34 | 96.45 |
| PLK1 | 98.83 | 97.02 |
| ROS/ROS1 | 97.82 | 95.23 |
| SYK | 98.13 | 97.43 |

The aforementioned description of the present invention is suggested for illustration, and those skilled in the art, to which the present invention pertains, may understand that it may be easily modified into other specific forms without modifying the technical scope or necessary features of the present invention. Thus, the embodiments described above shall be understood as being illustrative and not limitative in all aspects.

The invention claimed is:

1. An imidazole derivative of a following Formula 1 or a pharmaceutically acceptable salt thereof, wherein:

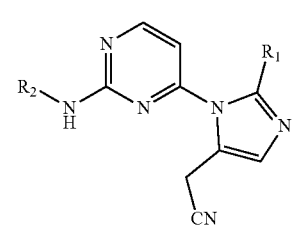

[Formula 1]

in the Formula 1 above,

R$_1$ is C$_4$-C$_{10}$ aryl, C$_4$-C$_{10}$ heteroaryl, or C$_4$-C$_{10}$ heterocycloalkyl, wherein C$_4$-C$_{10}$ aryl and C$_4$-C$_{10}$ heteroaryl are ones selected from the group consisting of phenyl, naphthyl, pyrenyl, carbazolyl, benzoxazolyl, benzodioxazolyl, 1,3-benzodioxolyl, 1,4-benzodioxinyl, benzothiazolyl, benzoimidazolyl, benzothiophenyl, quinolinyl, isoquinolinyl, indolyl, benzofuranyl, purinyl and indolizinyl, wherein C$_4$-C$_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein R$_1$ may be unsubstituted or substituted with at least one substituent selected from the group consisting of C$_1$-C$_6$ alkyl, C$_2$-C$_6$ alkenyl, C$_2$-C$_6$ alkynyl, C$_1$-C$_6$ alkoxy, C$_1$-C$_6$ haloalkyl, hydroxy, amino and halogen; and R$_2$ is C$_1$-C$_6$ alkyl, C$_2$-C$_6$ alkenyl, C$_2$-C$_6$ alkynyl, C$_2$-C$_6$ alkoxy, C$_2$-C$_6$ alcohol, C$_3$-C$_{10}$ cycloalkyl, or C$_4$-C$_{10}$ heterocycloalkyl, wherein C$_4$-C$_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl, and wherein R$_2$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino, halogen, $C_2$-$C_{10}$ alkylcarbonyl, and $C_4$-$C_{10}$ cycloalkylcarbonyl.

2. The imidazole derivative of the Formula 1 or the pharmaceutically acceptable salt thereof, according to claim 1, wherein:
$R_1$ is phenyl, naphthyl, 1,3-benzodioxolyl, quinolinyl, 2,3-dihydro-1,4 benzodioxinyl, or benzofuranyl,
wherein $R_1$ may be unsubstituted or substituted with at least one substituent selected from the group consisting of $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, hydroxy, amino and halogen; and
$R_2$ is $C_1$-$C_6$ alcohol, $C_3$-$C_{10}$ cycloalkyl, or $C_4$-$C_{10}$ heterocycloalkyl,
wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, piperidinyl and dihydrobenzodioxinyl,
and wherein $R_2$ may be unsubstituted or substituted with at least one substituent selected from the group consisting of $C_1$-$C_6$ alkyl, $C_1$-$C_6$ alkenyl, $C_1$-$C_6$ alkynyl, $C_1$-$C_6$ alkoxy, $C_1$-$C_6$ haloalkyl, hydroxy, amino, halogen, $C_2$-$C_{10}$ alkylcarbonyl, and $C_4$-$C_{10}$ cycloalkylcarbonyl.

3. The imidazole derivative of the Formula 1 or the pharmaceutically acceptable salt thereof, according to claim 1, wherein:
$R_1$ is phenyl, naphthyl, 1,3-benzodioxolyl, quinolinyl, 2,3-dihydro-1,4 benzodioxinyl, or benzofuranyl,
wherein $R_1$ may be unsubstituted or substituted with at least one substituent selected from the group consisting of $C_1$-$C_6$ alkyl, $C_1$-$C_6$ haloalkyl, and halogen; and
$R_2$ is $C_1$-$C_6$ alcohol, $C_3$-$C_{10}$ cycloalkyl, or $C_4$-$C_{10}$ heterocycloalkyl,
wherein $C_4$-$C_{10}$ heterocycloalkyl is one selected from the group consisting of tetrahydrofuranyl, tetrahydrothiophenyl, pyrrolidinyl, tetrahydropyranyl, tetrahydrothiopyranyl, and piperidinyl,
and wherein $R_2$ may be unsubstituted or substituted with at least one of $C_2$-$C_{10}$ alkylcarbonyl, or $C_4$-$C_{10}$ cycloalkylcarbonyl.

4. The imidazole derivative of the Formula 1 or the pharmaceutically acceptable salt thereof, according to claim 1, wherein:
$R_1$ is phenyl, naphthyl, 1,3-benzodioxolyl, quinolinyl, 2,3-dihydro-1,4 benzodioxinyl, or benzofuranyl,
wherein phenyl may be unsubstituted or substituted with at least one of $C_1$-$C_6$ haloalkyl, or halogen; and
$R_2$ is 2-hydroxypropyl, cyclohexyl, tetrahydropyranyl, or piperidinyl,
wherein piperidinyl may be unsubstituted or substituted with at least one of $C_4$-$C_{10}$ cycloalkylcarbonyl.

5. The imidazole derivative of the Formula 1 or the pharmaceutically acceptable salt thereof, according to claim 1, wherein:
$R_1$ is phenyl, naphthyl, 1,3-benzodioxolyl, quinolinyl, 2,3-dihydro-1,4 benzodioxinyl, or benzofuranyl,
wherein phenyl may be unsubstituted or substituted with at least one substituent selected from the group consisting of fluoro, chloro, and trifluoromethyl; and
R2 is 2-hydroxypropyl, cyclohexyl, tetrahydropyranyl, or piperidinyl,
wherein piperidinyl may be unsubstituted or substituted with cyclopropanecarbonyl.

6. The compound represented by the Formula 1 or the pharmaceutically acceptable salt thereof, according to claim 1, wherein
the imidazole derivative of the Formula 1 is:
2-(2-(benzo[d][1,3]dioxol-5-yl)-1-(2-(tetrahydro-2H-pyran-4-ylamino)pyrimidine-4-yl)-1H-imidazole-5-yl) acetonitrile;
2-(2-(2,3-dihydrobenzo[b][1,4]dioxin-6-yl)-1-(2-(tetrahydro-2H-pyran-4-ylamino)pyrimidine-4-yl)-1H-imidazole-5-yl)acetonitrile;
2-(2-(quinoline-2-yl)-1-(2-(tetrahydro-2H-pyran-4-ylamino)pyrimidine-4-yl)-1H-imidazole-5-yl)acetonitrile;
2-(2-(naphthalene-2-yl)-1-(2-(tetrahydro-2H-pyran-4-ylamino)pyrimidine-4-yl)-1H-imidazole-5-yl)acetonitrile;
2-(2-(3,4-dichlorophenyl)-1-(2-(tetrahydro-2H-pyran-4-ylamino)pyrimidine-4-yl)-1H-imidazole-5-yl)acetonitrile;
2-(2-(4-fluoro-3-(trifluoromethyl)phenyl)-1-(2-(tetrahydro-2H-pyran-4-ylamino)pyrimidine-4-yl)-1H-imidazole-5-yl)acetonitrile;
2-(2-(benzo[d][1,3]dioxol-5-yl)-1-(2-(cyclohexylamino)pyrimidine-4-yl)-1H-imidazole-5-yl)acetonitrile;
2-(1-(2-(cyclohexylamino)pyrimidine-4-yl)-2-(2,3-dihydrobenzo[b][1,4]dioxin-6-yl)-1H-imidazole-5-yl)acetonitrile;
2-(1-(2-(cyclohexylamino)pyrimidine-4-yl)-2-(quinoline-2-yl)-1H-imidazole-5-yl)acetonitrile;
2-(1-(2-(cyclohexylamino)pyrimidine-4-yl)-2-(naphthalene-2-yl)-1H-imidazole-5-yl)acetonitrile;
2-(1-(2-(cyclohexylamino)pyrimidine-4-yl)-2-(3,4-dichlorophenphenyl)-1H-imidazole-5-yl)acetonitrile;
2-(1-(2-(cyclohexylamino)pyrimidine-4-yl)-2-(4-fluoro-3-(trifluoromethyl)phenyl)-1H-imidazole-5-yl)acetonitrile;
2-(2-(benzo[d][1,3]dioxol-5-yl)-1-(2-(2-hydroxypropylamino)pyrimidine-4-yl)-1H-imidazole-5-yl)acetonitrile;
2-(2-(2,3-dihydrobenzo[b][1,4]dioxin-6-yl)-1-(2-(2-hydroxypropylamino)pyrimidine-4-yl)-1H-imidazole-5-yl)acetonitrile;
2-(1-(2-(2-hydroxypropylamino)pyrimidine-4-yl)-2-(quinoline-2-yl)-1H-imidazole-5-yl)acetonitrile;
2-(1-(2-(2-hydroxypropylamino)pyrimidine-4-yl)-2-(naphthalene-2-yl)-1H-imidazole-5-yl)acetonitrile;
2-(2-(3,4-dichlorophenyl)-1-(2-(2-hydroxypropylamino)pyrimidine-4-yl)-1H-imidazole-5-yl)acetonitrile;
2-(2-(4-fluoro-3-(trifluoromethyl)phenyl)-1-(2-(2-hydroxypropylamino)pyrimidine-4-yl)-1H-imidazole-5-yl)acetonitrile;
2-(2-(benzo[d][1,3]dioxol-5-yl)-1-(2-(piperidine-3-ylamino)pyrimidine-4-yl)-1H-imidazole-5-yl)acetonitrile;
2-(2-(2,3-dihydrobenzo[b][1,4]dioxin-6-yl)-1-(2-(piperidine-3-ylamino)pyrimidine-4-yl)-1H-imidazole-5-yl) acetonitrile;
2-(1-(2-(piperidine-3-ylamino)pyrimidine-4-yl)-2-(quinoline-2-yl)-1H-imidazole-5-yl)acetonitrile;
2-(2-(naphthalene-2-yl)-1-(2-(piperidine-3-ylamino)pyrimidine-4-yl)-1H-imidazole-5-yl)acetonitrile;
2-(2-(3,4-dichlorophenyl)-1-(2-(piperidine-3-ylamino) pyrimidine-4-yl)-1H-imidazole-5-yl)acetonitrile;

2-(2-(4-fluoro-3-(trifluoromethyl)phenyl)-1-(2-(piperi-
dine-3-ylamino)pyrimidine-4-yl)-1H-imidazole-5-yl)
acetonitrile;
2-(2-(benzo[d][1,3]dioxol-5-yl)-1-(2-(1-(cyclopropan-
ecarbonyl)piperidine-3-ylamino)pyrimidine-4-yl)-1H-
imidazole-5-yl)acetonitrile;
2-(1-(2-(1-(cyclopropanecarbonyl)piperidine-3-ylamino)
pyrimidine-4-yl)-2-(2,3-dihydrobenzo[b][1,4]dioxin-
6-yl)-1H-imidazole-5-yl)acetonitrile;
2-(1-(2-(1-(cyclopropanecarbonyl)piperidine-3-ylamino)
pyrimidine-4-yl)-2-(quinoline-2-yl)-1H-imidazole-5-
yl)acetonitrile;
2-(1-(2-(1-(cyclopropanecarbonyl)piperidine-3-ylamino)
pyrimidine-4-yl)-2-(naphthalene-2-yl)-1H-imidazole-
5-yl)acetonitrile;
2-(1-(2-(1-(cyclopropanecarbonyl)piperidine-3-ylamino)
pyrimidine-4-yl)-2-(3,4-dichlorophenyl)-1H-imida-
zole-5-yl)acetonitrile;
2-(1-(2-(1-(cyclopropanecarbonyl)piperidine-3-ylamino)
pyrimidine-4-yl)-2-(4-fluoro-3-(trifluoromethyl)phe-
nyl)-1H-imidazole-5-yl)acetonitrile; or
2-(2-(benzofuran-5-yl)-1-(2-(1-cyclopropanecarbonyl)pi-
peridine-3-ylamino)pyrimidine-4-yl)-1H-imidazole-5-
yl)acetonitrile.

7. A method for preparing the imidazole derivative of claim 1, as shown in a following Reaction Formula 1, comprising steps of:
performing a Buchwald amination coupling reaction between the compound of the Formula I and 4-chloro-2-(methylthio)pyrimidine to prepare a compound of a Formula II (Step 1);
oxidizing the compound of the Formula II prepared in the Step 1 to prepare a compound of a Formula III (Step 2); and
substituting a methylsulfonyl group of the compound of the Formula III prepared in the Step 2 with an amine group to prepare a compound of a Formula IV (Step 3)

[Reaction Formula 1]

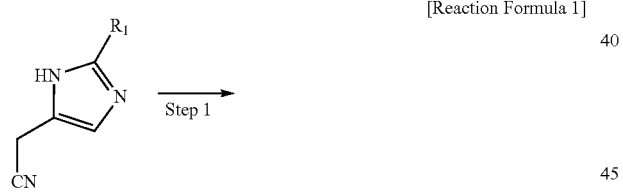

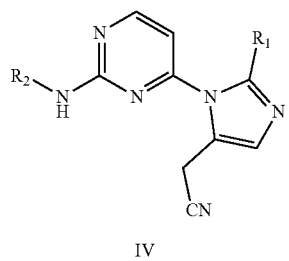

wherein in the Formulas I to IV, R1 and R2 are as defined in the Formula 1 of claim 1.

8. The method of claim 7, further comprising Reaction Formula 2 comprising a step of:
performing a deprotection of the compound of the Formula IV-4 prepared in the Step 3 to prepare a compound of a Formula V (Step 4)

[Reaction Formula 2]

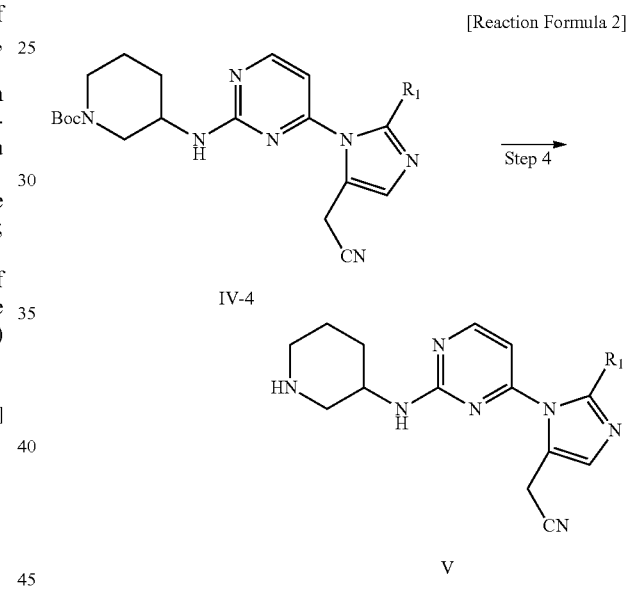

wherein in the Formulas IV-4 and V, R1 is as defined in claim 7.

9. The method of claim 8, further comprising Reaction Formula 3 comprising a step of:
acylating the compound of the Formula V prepared in the Step 4 to prepare a compound of a Formula VI (Step 5)

[Reaction Formula 3]

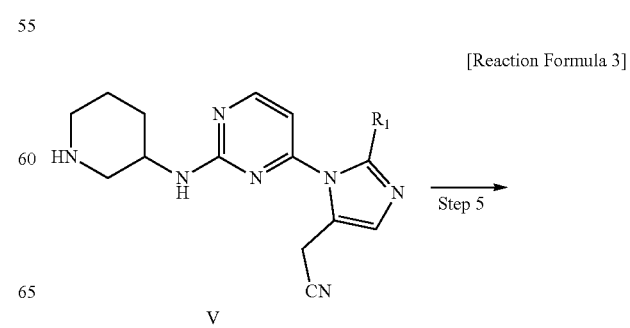

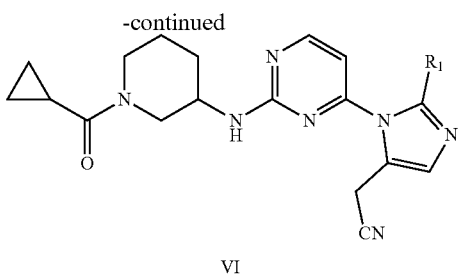

VI wherein in 4 the Formulas V and VI, R1 is as defined in claim 8.

10. A pharmaceutical composition, comprising the imidazole derivative of claim 1 or the pharmaceutically acceptable salt thereof as an effective component, for the treatment of degenerative brain nervous system diseases related to the inhibition of C-Jun N-terminal kinase.

11. The pharmaceutical composition, according to claim 10, characterized in that the above degenerative brain nervous system diseases are selected from the group consisting of Alzheimer's disease, Parkinson's disease, Huntington's disease, multiple sclerosis and stroke.

12. The pharmaceutical composition, according to claim 10, characterized in that the above composition inhibits an activity of one selected from the group consisting of C-Jun N-terminal kinase 1 (JNK 1), C-Jun N-terminal kinase 2 (JNK 2) and C-Jun N-terminal kinase 3 (JNK 3).

13. A method for treating degenerative brain nervous system diseases related to the inhibition of C-Jun-N-terminal kinase, comprising a step of administering a therapeutically effective amount of the imidazole derivative of claim 1 or the pharmaceutically acceptable salt thereof into an individual.

* * * * *